US005736121A

United States Patent [19]

Unger

[11] Patent Number: 5,736,121
[45] Date of Patent: Apr. 7, 1998

[54] STABILIZED HOMOGENOUS SUSPENSIONS AS COMPUTED TOMOGRAPHY CONTRAST AGENTS

[75] Inventor: Evan C. Unger, Tucson, Ariz.

[73] Assignee: ImaRx Pharmaceutical Corp., Tucson, Ariz.

[21] Appl. No.: 444,754

[22] Filed: May 19, 1995

Related U.S. Application Data

[63] Continuation-in-part of Ser. No. 247,656, May 23, 1994, abandoned.

[51] Int. Cl.⁶ .......................... A61K 49/04; A61B 5/055
[52] U.S. Cl. .............................. 424/9.4; 424/9.32
[58] Field of Search ....................... 424/9.4, 9.32, 424/9.52, 9.51, 9.5, 450, 455; 128/662.02; 427/213.3; 514/937

[56] References Cited

U.S. PATENT DOCUMENTS

| | | | |
|---|---|---|---|
| 3,015,128 | 1/1962 | Somerville, Jr. | 18/2.6 |
| 3,293,114 | 12/1966 | Kenaga et al. | 162/168 |
| 3,479,811 | 11/1969 | Walters | 57/153 |
| 3,488,714 | 1/1970 | Walters et al. | 161/161 |
| 3,532,500 | 10/1970 | Priest et al. | 96/91 |
| 3,594,326 | 7/1971 | Himmel | 252/316 |
| 3,615,972 | 10/1971 | Morehouse, Jr. et al. | 156/79 |
| 3,732,172 | 5/1973 | Herbig et al. | 252/316 |
| 3,873,564 | 3/1975 | Schneider et al. | 260/309.6 |
| 3,945,956 | 3/1976 | Garner | 260/2.5 B |
| 3,960,583 | 6/1976 | Netting et al. | 106/122 |
| 4,089,801 | 5/1978 | Schneider | 252/316 |
| 4,108,806 | 8/1978 | Cohrs et al. | 521/54 |
| 4,138,383 | 2/1979 | Rembaum et al. | 260/29.7 H |
| 4,162,282 | 7/1979 | Fulwyler et al. | 264/9 |
| 4,179,546 | 12/1979 | Garner et al. | 521/56 |
| 4,192,859 | 3/1980 | Mackaness et al. | 424/5 |
| 4,224,179 | 9/1980 | Schneider | 252/316 |
| 4,229,360 | 10/1980 | Schneider et al. | 260/403 |
| 4,276,885 | 7/1981 | Tickner et al. | 128/660 |
| 4,310,505 | 1/1982 | Baldeschwieler et al. | 424/1 |
| 4,310,506 | 1/1982 | Baldeschwieler et al. | 424/1 |
| 4,315,514 | 2/1982 | Drewes et al. | 128/653 |
| 4,331,654 | 5/1982 | Morris | 424/38 |
| 4,344,929 | 8/1982 | Bonsen et al. | 424/15 |
| 4,420,442 | 12/1983 | Sands | 264/13 |
| 4,421,562 | 12/1983 | Sands | 106/75 |
| 4,426,330 | 1/1984 | Sears | 260/403 |
| 4,428,924 | 1/1984 | Millington | 424/4 |
| 4,442,843 | 4/1984 | Rasor et al. | 128/660 |
| 4,466,442 | 8/1984 | Hilmann et al. | 128/653 |
| 4,533,254 | 8/1985 | Cook et al. | 366/176 |
| 4,534,899 | 8/1985 | Sears | 260/403 |
| 4,540,629 | 9/1985 | Sands et al. | 428/402 |
| 4,544,545 | 10/1985 | Ryan et al. | 424/1.1 |
| 4,549,892 | 10/1985 | Baker et al. | 65/21.4 |
| 4,569,836 | 2/1986 | Gordon | . |
| 4,572,203 | 2/1986 | Feinstein | 128/661 |
| 4,586,512 | 5/1986 | Do-huu et al. | 128/660 |
| 4,603,044 | 7/1986 | Geho et al. | 424/9 |
| 4,615,879 | 10/1986 | Runge et al. | 424/9 |

(List continued on next page.)

FOREIGN PATENT DOCUMENTS

| | | |
|---|---|---|
| B-30351/89 | 3/1993 | Australia. |
| 0 107 559 | 5/1984 | European Pat. Off.. |
| 0077752 B1 | 3/1986 | European Pat. Off.. |
| 0 243 947 | 4/1987 | European Pat. Off.. |
| 0 231 091 | 8/1987 | European Pat. Off.. |
| 0 272 091 | 6/1988 | European Pat. Off.. |
| 0 320 433 A2 | 12/1988 | European Pat. Off.. |
| 0 324 938 | 7/1989 | European Pat. Off.. |
| 0 338 971 | 10/1989 | European Pat. Off.. |
| 357163 A1 | 3/1990 | European Pat. Off.. |
| 0 361 894 | 4/1990 | European Pat. Off.. |
| 0 216 730 | 1/1991 | European Pat. Off.. |
| 0 467 031 A2 | 5/1991 | European Pat. Off.. |
| 441468 A2 | 8/1991 | European Pat. Off.. |
| 0 357 164 B1 | 10/1991 | European Pat. Off.. |
| 0 458 745 A1 | 11/1991 | European Pat. Off.. |
| 0 314 764 B1 | 9/1992 | European Pat. Off.. |
| 0 554 213 A1 | 8/1993 | European Pat. Off.. |
| 0 727 225 A2 | 8/1996 | European Pat. Off.. |
| 62-286534 | 12/1987 | Japan. |
| 63-60943 | 3/1988 | Japan. |
| 1044680 | 10/1966 | United Kingdom. |
| 2193095 | 2/1988 | United Kingdom. |
| WO 80/02365 | 11/1980 | WIPO. |
| WO 82/01642 | 5/1982 | WIPO. |
| 85/01161 | 3/1985 | WIPO. |

(List continued on next page.)

OTHER PUBLICATIONS

Chang et al., "Semipermeable Aqueous Microcapsules", *Canadian J. Of Phys. And Pharm.*, 1966, 44, 115–128.

Chang, "Semipermeable Microcapsules", *Science*, 1964, 146, 524–525.

Deasy, Microencapsulation and Related Drug Processes, 1983, vol. 20, Chs. 9 and 10, 195–240 (Marcel Dekker, Inc., NY).

Yeung et al., "Preparation of Microencapsulated Liposomes", *J. Microencapsulation*, 1988, 5, 331–337.

Mattrey et al., Gas Emulsions as Ultrasound Contrast Agents; Preliminary Results in Rabbits and Dogs, *Investigative Radiology*, vol. 29, Jun. Supp. 2, pp. S139–S141, 1994.

Meltzer et al., Transmission of Ultrasonic Contrast Through the Lungs, *Ultrasound in Med. & Biol.*, vol. 7, No. 4, 377–384, 1981.

PR Newswire, Apr. 1, 1986.

Swanson et al., Chapter 22, "Enhancement Agents for Ultrasound: Fundamentals", *Pharmaceuticals In Medical Imaging*, pp. 682–687 (1990).

(List continued on next page.)

Primary Examiner—Gary E. Hollinden
Assistant Examiner—Michael G. Hartley
Attorney, Agent, or Firm—Woodcock Washburn Kurtz Mackiewicz & Norris LLP

[57] ABSTRACT

Novel stabilized suspensions of a gas as diagnostic contrast agents, including computed tomography (CT) and magnetic resonance (MR) contrast agents. In preferred embodiments, the suspensions comprise stabilized gas filled microspheres. Also in some preferred embodiments, at least a portion of the gas is derived from a gaseous precursor.

31 Claims, No Drawings

U.S. PATENT DOCUMENTS

| | | | |
|---|---|---|---|
| 4,620,546 | 11/1986 | Aida et al. | 128/660 |
| 4,646,756 | 3/1987 | Watmough et al. | 128/804 |
| 4,657,756 | 4/1987 | Rasor et al. | 424/9 |
| 4,658,828 | 4/1987 | Dory | 128/660 |
| 4,675,310 | 6/1987 | Chapman et al. | 514/6 |
| 4,681,119 | 7/1987 | Rasor et al. | 128/660 |
| 4,684,479 | 8/1987 | D'Arrigo | 252/307 |
| 4,689,986 | 9/1987 | Carson et al. | 73/19 |
| 4,718,433 | 1/1988 | Feinstein | 128/660 |
| 4,728,575 | 3/1988 | Gamble et al. | 428/402.2 |
| 4,728,578 | 3/1988 | Higgins et al. | 428/462 |
| 4,731,239 | 3/1988 | Gordon | 424/9 |
| 4,737,323 | 4/1988 | Martin et al. | 264/4.3 |
| 4,774,958 | 10/1988 | Feinstein | 128/660.01 |
| 4,775,522 | 10/1988 | Clark, Jr. | 424/9 |
| 4,776,991 | 10/1988 | Farmer et al. | 264/4.3 |
| 4,781,871 | 11/1988 | West, III et al. | 264/4.3 |
| 4,789,501 | 12/1988 | Day et al. | 252/645 |
| 4,790,891 | 12/1988 | Halliday et al. | 149/2 |
| 4,822,534 | 4/1989 | Lencki et al. | 264/4.3 |
| 4,830,858 | 5/1989 | Payne et al. | 424/450 |
| 4,844,882 | 7/1989 | Widder et al. | 424/9 |
| 4,863,717 | 9/1989 | Keana | 424/9 |
| 4,865,836 | 9/1989 | Long, Jr. | 424/5 |
| 4,877,561 | 10/1989 | Iga et al. | 264/4.3 |
| 4,893,624 | 1/1990 | Lele | 128/399 |
| 4,895,719 | 1/1990 | Radhakrishnan | 424/45 |
| 4,898,734 | 2/1990 | Mathiowitz et al. | 424/426 |
| 4,900,540 | 2/1990 | Ryan et al. | 424/9 |
| 4,921,706 | 5/1990 | Roberts et al. | 424/450 |
| 4,927,623 | 5/1990 | Long, Jr. | 424/5 |
| 4,938,947 | 7/1990 | Nicolau et al. | 424/1.1 |
| 4,957,656 | 9/1990 | Cerny et al. | 252/311 |
| 4,981,692 | 1/1991 | Popescu et al. | 424/422 |
| 4,985,550 | 1/1991 | Charpiot et al. | 536/18.4 |
| 4,987,154 | 1/1991 | Long, Jr. | 514/772 |
| 4,993,415 | 2/1991 | Long | 128/653 |
| 4,996,041 | 2/1991 | Arai et al. | 424/9 |
| 5,000,960 | 3/1991 | Wallach | 424/450 |
| 5,008,050 | 4/1991 | Cullis et al. | 264/4.3 |
| 5,013,556 | 5/1991 | Woodle et al. | 424/450 |
| 5,019,370 | 5/1991 | Jay et al. | 424/4 |
| 5,045,304 | 9/1991 | Schneider et al. | 424/9 |
| 5,049,388 | 9/1991 | Knight et al. | 424/450 |
| 5,078,994 | 1/1992 | Nair et al. | 424/501 |
| 5,088,499 | 2/1992 | Unger | 128/662.2 |
| 5,114,703 | 5/1992 | Wolf et al. | 424/5 |
| 5,123,414 | 6/1992 | Unger | 128/654 |
| 5,137,928 | 8/1992 | Erbel et al. | 521/56 |
| 5,141,738 | 8/1992 | Rasor et al. | 424/2 |
| 5,147,631 | 9/1992 | Glajch et al. | 424/9 |
| 5,149,319 | 9/1992 | Unger | 604/22 |
| 5,171,755 | 12/1992 | Kaufman | 514/759 |
| 5,186,922 | 2/1993 | Shell et al. | 128/654 |
| 5,190,982 | 3/1993 | Erbel et al. | 521/56 |
| 5,194,266 | 3/1993 | Abra et al. | 424/450 |
| 5,195,520 | 3/1993 | Schlief et al. | 128/660.02 |
| 5,196,183 | 3/1993 | Yudelson et al. | 424/9 |
| 5,198,225 | 3/1993 | Meybeck et al. | 424/450 |
| 5,205,287 | 4/1993 | Erbel et al. | 128/632 |
| 5,205,290 | 4/1993 | Unger | 128/653.4 |
| 5,209,720 | 5/1993 | Unger | 604/22 |
| 5,213,804 | 5/1993 | Martin et al. | 424/450 |
| 5,215,680 | 6/1993 | D'Arrigo | 252/307 |
| 5,219,538 | 6/1993 | Henderson et al. | 428/402.2 |
| 5,228,446 | 7/1993 | Unger et al. | 128/662.02 |
| 5,230,882 | 7/1993 | Unger | 424/9 |
| 5,271,928 | 12/1993 | Schneider et al. | 424/9 |
| 5,281,408 | 1/1994 | Unger | 424/4 |
| 5,305,757 | 4/1994 | Unger et al. | 128/662.02 |
| 5,310,540 | 5/1994 | Giddey et al. | 424/9 |
| 5,315,997 | 5/1994 | Widder et al. | 128/653.3 |
| 5,316,771 | 5/1994 | Barenholz et al. | 424/450 |
| 5,334,381 | 8/1994 | Unger | 424/9 |
| 5,344,930 | 9/1994 | Riess et al. | 544/84 |
| 5,350,571 | 9/1994 | Kaufman et al. | 424/9 |
| 5,352,435 | 10/1994 | Unger | 424/9 |
| 5,358,702 | 10/1994 | Unger | 424/9 |
| 5,362,478 | 11/1994 | Desai et al. | 424/9 |
| 5,380,519 | 1/1995 | Schneider et al. | 424/9 |
| 5,393,524 | 2/1995 | Quay | 424/9 |
| 5,409,688 | 4/1995 | Quay | 424/9 |
| 5,410,516 | 4/1995 | Uhlendorf et al. | 367/7 |
| 5,413,774 | 5/1995 | Schneider et al. | 424/9.51 |
| 5,425,366 | 6/1995 | Reinhardt et al. | 128/662.02 |
| 5,433,204 | 7/1995 | Olson | 128/661.08 |
| 5,445,813 | 8/1995 | Schneider et al. | 424/9.51 |
| 5,456,900 | 10/1995 | Unger | 424/9.4 |
| 5,469,854 | 11/1995 | Unger et al. | 128/662.02 |
| 5,470,582 | 11/1995 | Supersaxo et al. | 424/489 |
| 5,487,390 | 1/1996 | Cohen et al. | 128/662.02 |
| 5,496,535 | 3/1996 | Kirkland | 424/9.37 |
| 5,498,421 | 3/1996 | Grinstaff et al. | 424/450 |
| 5,505,932 | 4/1996 | Grinstaff et al. | 424/9.3 |
| 5,527,521 | 6/1996 | Unger | 424/93 |
| 5,529,766 | 6/1996 | Klaveness et al. | 424/9.52 |
| 5,531,980 | 7/1996 | Schneider et al. | 424/9.52 |
| 5,536,489 | 7/1996 | Lohrmann et al. | 424/9.52 |
| 5,536,490 | 7/1996 | Klaveness et al. | 424/9.52 |
| 5,540,909 | 7/1996 | Schutt | 424/9.52 |
| 5,547,656 | 8/1996 | Unger | 424/9.4 |
| 5,552,133 | 9/1996 | Lambert et al. | 424/9.52 |
| 5,556,610 | 9/1996 | Yan et al. | 424/9.52 |
| 5,558,094 | 9/1996 | Quay | 128/662.02 |
| 5,558,853 | 9/1996 | Quay | 424/9.5 |
| 5,558,854 | 9/1996 | Quay | 424/9.52 |
| 5,558,855 | 9/1996 | Quay | 424/9.5 |
| 5,560,364 | 10/1996 | Porter | 128/662.02 |
| 5,562,893 | 10/1996 | Lohrmann | 424/9.52 |
| 5,567,413 | 10/1996 | Klaveness et al. | 424/9.51 |
| 5,567,414 | 10/1996 | Schneider et al. | 424/9.52 |
| 5,567,765 | 10/1996 | Moore et al. | 524/801 |
| 5,573,751 | 11/1996 | Quay | 424/9.52 |
| 5,578,292 | 11/1996 | Schneider et al. | 424/9.51 |
| 5,585,112 | 12/1996 | Unger et al. | 424/450 |
| 5,595,723 | 1/1997 | Quay | 424/9.5 |
| 5,606,973 | 3/1997 | Lambert et al. | 128/662.02 |
| B1 4,229,360 | 11/1991 | Schneider et al. | 260/403 |

FOREIGN PATENT DOCUMENTS

| | | |
|---|---|---|
| WO 86/00238 | 1/1986 | WIPO . |
| WO 86/01103 | 2/1986 | WIPO . |
| WO 89/05040 | 6/1989 | WIPO . |
| WO 90/01952 | 3/1990 | WIPO . |
| WO 90/04384 | 5/1990 | WIPO . |
| WO 90/04943 | 5/1990 | WIPO . |
| WO 91/00086 | 1/1991 | WIPO . |
| WO 91/12823 | 9/1991 | WIPO . |
| WO 91/15244 | 10/1991 | WIPO . |
| WO 92/10166 | 6/1992 | WIPO . |
| WO 92/11873 | 7/1992 | WIPO . |
| WO 92/17212 | 10/1992 | WIPO . |
| WO 92/17213 | 10/1992 | WIPO . |
| WO 92/17436 | 10/1992 | WIPO . |
| WO 92/21382 | 12/1992 | WIPO . |
| WO 93/00933 | 1/1993 | WIPO . |
| WO 93/05819 | 1/1993 | WIPO . |
| WO 93/06869 | 4/1993 | WIPO . |
| WO 93/13809 | 7/1993 | WIPO . |
| WO 93/17718 | 9/1993 | WIPO . |
| WO 93/20802 | 10/1993 | WIPO . |
| WO 94/06477 | 3/1994 | WIPO . |

| | | |
|---|---|---|
| WO 94/09829 | 5/1994 | WIPO . |
| WO 94/16739 | 8/1994 | WIPO . |
| WO 94/21302 | 9/1994 | WIPO . |
| WO 94/28780 | 12/1994 | WIPO . |
| WO 95/06518 | 3/1995 | WIPO . |
| WO 95/07072 | 3/1995 | WIPO . |
| WO 95/23615 | 9/1995 | WIPO . |
| WO 96/04018 | 2/1996 | WIPO . |
| WO 96/09793 | 4/1996 | WIPO . |
| WO 96/36286 | 11/1996 | WIPO . |

OTHER PUBLICATIONS

Ophir et al., "Contrast Agents in Diagnostic Ultrasound", *Ultrasound in Med. & Biol.*, vol. 15, No. 4, pp. 319–333 (1989).

Jacobs, "Intraocular gas measurement using A–scan ultrsound", *Current Eye Research*, vol. 5, No. 8, pp. 575–578 (1986).

Dittrich, "Cardiac Muscle Ischemia and Infarction", *The Second Annual International Symposium on Contrast Agents in Diagnostic Ultrasound*, Atlantic City, NJ (May 7, 1996) (abstract).

Pantely, "Intravenous Contrast Echocardiography-Tissue Imaging & Quantification of Coronary Blood Flow", *The Second Annual International Symposium on Contrast Agents in Diagnostic Ultrasound*, Atlantic City, NJ (May 7, 1996) (abstract).

Schutt et al., "Osmotically Stabilized Microbubble Sonographic Contrast Agents", *Acad. Radiol.*, vol. 3, Suppl. 2, pp. S188–S190 (Aug. 1996).

Frézard, et al., "Permeability and stability in buffer and in human serum of fluorinated phospholipid–based liposomes", *Biochimica et Biophysica Acta*, 1192, pp. 61–70 (1994).

Frézard, et al., "Fluorinated Phospholipid–Based Vesicles as Potential Drug Carriers: Encapsulation/Sustaining of Drugs and Stability in Human Serum", *Art, Cells, Blood Subs., and Immob. Biotech.*, 22(4), pp. 1403–1408 (1994).

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry*, vol. 13, No. 3, pp. 568–574 (1974).

Thanassi, "Aminomalonic Acid: Spontaneous Decarboxylation and Reaction with 5–Deoxypyridoxal", *Biochemistry*, vol. 9, No. 3, pp. 525–532 (1970).

Stelmashok et al., *Koordinatsionnaya Khimiya*, vol. 3, No. 4, pp. 524–527 (1977) (Russian and English language versions).

Mayhew et al., "High–Pressure Continuous–Flow System for Drug Entrapment in Liposomes", *Methods in Enzymology*, vol. 149, pp. 64–77 (1987).

Mayhew et al., "Characterization of Liposomes Prepared Using a Microemulsifier", *Biochimica et Biophysica Acta*, vol. 775, pp. 169–174 (1984).

Hope et al., "Production of Large Unilamellar Vesicles by a Rapid Extrusion Procedure: Characterization of Size Distribution, Trapped Volume, and Ability to Maintain a Membrane Potential", *Biochimica et Biophysica Acta*, 812: 55–65 (1985).

Mayer et al., "Vesicles of Variable Size Produced by a Rapid Extrusion Procedure", *Biochimica et Biophysica Acta*, vol. 858, pp. 161–168 (1986).

Cheng, et al., "The Production and Evaluation of Contrast–Carrying Liposomes Made with an Automatic High Pressure System", *Investigative Radiology*, vol. 22, pp. 47–55 (1987).

Jain, et al., *Introduction to Biological Membranes*, Ch. 9, pp. 192–231 (J. Wiley and Sons, N.Y. 1980).

Sigel, H., ed., *Metal Ions in Biological Systems: Antibiotics and Their Complexes*, vol. 19 (Marcel Dekker, N.Y. 1985).

Nayar et al., "Generation of Large Unilamellar Vesicles From Long–chain Saturated Phosphatidylcholines by Extrusion Technique", *Biochimica et Biophysica Acta*, vol. 986, pp. 200–206 (1989).

Hope et al., "Generating of Multilamellar and Unilamellar Phospholipid Vesicles", *Chemistry and Physics of Lipids*, vol. 40, pp. 89–107 (1986).

Mattrey et al., "Perfluorochemicals as US Contrast Agents for Tumpr–Imaging and Hepatosplenography: Preliminary Clinical Results", *Radiology*, vol. 163, pp. 339–343 (1987).

Mattrey et al., "Perfluoroctylbromide: A Liver/Spleen–Specific and Tumor Imaging Ultrasound Contrast Material", *Radiology*, vol. 145, pp. 759–762 (1982).

Keller et al., "Successful Left Ventricular Opacification Following Peripheral Venous Injection of Sonicated Contrast Agent: An Experimental Evaluation", *LV Contrast Echocardiography*, vol. 114, No. 3, pp. 570–575 (1987).

Feinstein et al., "Two–Dimensional Contrast Echocardiography, I: In Vitro Development and Quantitative Analysis of Echo Contrast Agents", *JACC*, vol. 3, No. 1, pp. 14–20 (1984).

Ten Cate et al., "Two–Dimensional Contrast Echocardiography, II: Transpulmonary Studies", *JACC*, vol. 3, No. 1, pp. 21–27 (1984).

Unger et al., "Hepatic Metastases: Liposomal Gd–DTPA–enhanced MR Imaging", *Radiology*, vol. 171, pp. 81–85 (1989).

Deamer et al., "Permeability of Lipid Bilayers to Water and Ionic Solutes", *Chemistry and Physics of Lipids*, vol. 40, pp. 167–188 (1986).

Gutknecht et al., "Diffusion of Carbon Dioxide Through Lipid Bilayer Membranes: Effect of Carbonic Anhydrase, Bicarbonate, and Unstirred Layers", *Chemical Abstracts*, 87:34772q (1977).

Scarpa et al., "Cation Permeability of Liposomes as a Function of the Chemical Composition of the Lipid Bilayers", *Biochimica et Biophysica Acta*, vol. 241, pp. 789–797 (1971).

MacNaughton et al., "Effects of Gaseous Anesthetics and Inert Gases on the Phase Transition in Smectic Mesophases of Dipalmitoyl Phosphatidylcholine", *Biochimica et Biophysica Acta*, vol. 597, pp. 193–198 (1980).

Tilcock et al., "Liposomal Gd–DTPA: Preparation and Characterization of Relaxivity", *Radiology*, vol. 171, pp. 77–80 (1989).

Mann et al., "Formation of Iron Oxides in Unilamellar Vesicles", *Journal of Colloid and Interface Science*, vol. 122, No. 2, pp. 326–335 (1988).

Anderson et al., "Manganese (III) Complexes in Oxidative Decarboxylation of Acids", *J. Am. Chem. Soc.*, vol. 92, No.8, pp. 2450–2460 (1970).

Muhlradt et al., "Vitamin B6 Analogs: An Improved Synthesis of 5–Deoxypyridoxal", *New Compounds*, vol. 10, pp. 129–130 (1967).

Chapman D., "Physiochemical Properties of Phospholipids and Lipid Water Systems", *Liposome Technology*, Gregoriadis, G., ed., vol. 1, pp. 1–19 (CRC Press, Boca Raton, FL, 1984).

Violante et al., "Particulate Suspensions as Ultrasonic Contrast Agents for Liver and Spleen", *Inv. Rad.*, vol. 23, pp. S294–S297, Sep. 1988.

Fritzsch et al., "Preclinical and Clinical Results with an Ultrasonic Contrast Agent", *Inv. Rad.*, vol. 23, pp. S302–S305, Sep. 1988.

Brochure, *Experience*, Sonicator™, Heat Systems–Ultrasonics, Inc. (1987).

M. Ostro, "Liposomes", Marcel Dekker, New York, pp. 102–103 (1983).

Fukuda et al., "Polymer–Encased Vesicles Derived from Diotadecyldimethylammonium Methacrylate", *J. Am. Chem. Soc.*, vol. 108, pp. 2321–2327 (1986).

Regen, "Polymerized Vesicles", *J. Am. Chem. Soc.*, vol. 102, pp. 6638–6640 (1989).

Rose, A. and Rose, E., "The Condensed Chemical Dictionary", Reinhold Publishing, New York, pp. 728 and 743 (1966).

A.G. Belykh, *Farmakol Toksikol.* (MOSC), vol. 44(3), pp. 322–326 (1981) (abstract).

J. Vion–Dury et al., *J. Pharmacol. Exper. Ther.*, vol. 250(3), pp. 1113–1118 (1989) (abstract).

M.R. Zalutsky et al., *Invest. Radiol.*, vol. 22(2), pp. 141–147 (1987) (abstract).

Crowe et al., *Archives of Biochemistry and Biophysics*, vol. 242, pp. 240–247 (1985).

Crowe et al., *Archives of Biochemistry and Biophysics*, vol. 220, pp. 477–484 (1983).

Dorland's Illustrated Medical Dictionary, p. 946, 27th ed. (W.B. Saunders Company, Philadelphia 1988).

*Liposome Technology*, Gregoriadis, G., ed., vol. I, pp. 1–18, 29–35, 51–65 and 79–107 (CRC Press Inc., Boca Raton, FL, (1984).

Madden et al., *Chemistry and Physics of Lipids*, vol. 53, pp. 37–46 (1990).

Sinkula et al., *J. Pharm. Sci.*, vol. 64, pp. 181–210 (1975).

Shiina et al., "Hyperthermiaby Low–frequency Synthesized Ultrasound", *IEEE Engineering*, pp. 879–880, vol. 2 (abstract), (1987).

McAvoy et al., *IEEE Engineering, Ultrasonics Symposium Proceedings*, vol. 2, pp. 677–1248 (abstract) (1989).

Chapman et al., "Biomembrane Phase Transitions", *J. Biol. Chem.*, 1974, 249:2512–2521.

Hug et al., "Liposomes for the Transformation of Eukaryotic Cells", *Biochimica et Biophysica Acta*, 1991, 1097:1–17.

Marsh, *CRC Handbook of Lipid Bilayers* (CRC Press, Boca Raton, FL 1990) pp. 139–141.

Szoka et al., "Procedure for Preparation of Liposomes With Large Internal Aqueous Space . . . ", *Proc. Natl. Acad. Sci.* 1978, 75:4194–4198.

Acoustic Imaging; AI5200; Convex Curved Linear Array Ultrasound Transducers Operator's Manual, Nov. 20, 1989, 4700–0003–1C, p. 4.

Bangham et al., "Diffusion of Univalent Ions across the Lamellae of Swollen Phospholipids", *J. Mol. Biol.*, 1965, 13:238–252.

Carson et al., *Ultrasound in Med. & Biol.* 3, 1978, 341–350.

Chiellini et al., *Polymers in Medicine II: Biomedical and Pharmaceutical Applications*, (Plenum Press, New York and London) pp. 387–396 (1983).

deGier et al., "Relations Between Liposomes and Biomembranes", *Annals of The New York Academy of Sciences*, 1978, 308:85–99.

Felgner et al., "Lipofection: A highly efficient, lipid–mediated DNA–transfection procedure", *Proc. Natl. Acad. Sci.*, 1987, 84:7413–7417.

Gabizon et al., "Liposome formulations with prolonged circulation time in blood and enhanced uptake by tumors", *Proc. Natl. Acad. Sci.*, 1988, 85:6949–6953.

Garelli, et al., *Biochimica et Biophysica Acta*, vol. 1127:41–48 (1992).

Kawai et al., "New Procedure for DNA Transfection with Polycation and Dimethyl Sulfoxide", *Molecular and Cellular Biology*, 1984, 4:1172–1174.

Kuo et al., "Metallocene Antitumor Agents. Solution and Solid–State Molybdenocene Coordination . . . ", *J. Am. Chem. Soc.*, 1991, 113:9027–9045.

*Mammalian Cell Biotechnology: A Practical Approach*, M. Butler, 1991 (Oxford University Press, New York), pp. 57–70.

Mathiowitz et al., "Photochemical Rupture of Microcapsules: A Model System", *Journal of Applied Polymer Science*, 1981, 26:809–822.

May et al., "Cationic Liposomes Enable Bovine Herpesvirus Type 2 DNA to Infect Cells", *Acta virol.*, 1991, 35:107.

Poznansky et al., "Biologica Approaches to the Controlled Delivery of Drugs: A Critical Review", *Pharmacol, Rev.*, 1984, 36:277–336.

Sato et al., "Recent Aspects in the Use of Liposomes in Biotechnology and Medicine", *Prog. Lipid Res.* 1992, 4:345–372.

Simons et al., "Antisense c–myb oligonucleotides inhibit intimal arterial smooth muscle cell accumulation in vivo", *Nature*, 1992, 359:67–70.

Thompson, Larry, "At Age 2, Gene Therapy Enters a Growth Phase", *Science* 1992, 258:744–746.

Trubetskoy et al., "Cationic liposomes enhance targeted delivery and expression of exogenous DNA . . . ", Biochimica et Biophysica Acta 1992, 131:311–313.

Umemura et al., "Studies on Sonodynamic Cancer Therapy", *IEEE*, 1992, O–7803–0785, pp. 354–355.

Williams, "Human Gene Therapy: Searching for Better Vectors", *ASM News* [American Society for Microbology] 1992, 58:67–69.

Woodle et al., "Versatility in lipid compositions showing prolonged circulation . . . ", *Biochimica et Biophysica Acta* 1992, 1105:193–200.

Zhou et al., "Targeted delivery of DNA by liposomes and polymers", *J. of Controlled Release* 1992, 19:269–274.

Mathiowitz et al., "Polyanhydride Microspheres as Drug Carriers", *Journal of Applied Polymer Science*, vol. 35, pp. 755–774 (1988).

Sankaram et al., "Cholesterol–Induced Fluid–Phase Immiscibility in Membranes", *Proc. Natl. Acad. Sci.*, vol. 88, pp. 8686–8690 (1991).

*Scientific Apparatus Catalog 92/93* (VWR Scientific, 1991), "Syringes", pp. 1511–1513; Filtration, Syringe Filters, pp. 766–768; Filtration, Membranes, pp. 750–753; Filtration, Filter Holders, p. 744, (1991).

Gramiak et al., *Radiology*, "Detection of Intracardiac Blood Flow by Pulsed Echo–Ranging", pp. 415–418 (1971).

Feigenbaum et al., *Circulation*, "Identification of Ultrasound Echoes from the Left Ventricle by Use of Intracardiac Injections of Indocyanine Green", vol. XL1, pp. 615–621 (1970).

Santaella, et al., *FEBS* 13463, "Extended In Vivo Blood Circulation Time of Fluorinated Liposomes", vol. 336, No. 3, pp. 481–484 (1993).

Kost, et al, *Polymers in Medicine II*, "Ultrasonic Modulated Drug Delivery Systems, pp. 387–396 (1988).

Brown and Langer, *Annual Review Medicine*, 1988, 39:221 29, Annual Review, Inc., "Transdermal Delivery of Drugs", pp. 221–229.

Moseley, et al., *Microbubbles: A Novel MR Susceptibility Contrast Agent*, abstract, 1991 Napa, California Meeting of the Society for Magnetic Resonance in Medicine.

Ter–Pogossian, *Physical Principles and Instrumentation*, "Computed Body Tomography", Chapter 1, pp. 1–7, (1985).

Aronberg, *Techniques*, "Computed Body Tomography", Chapter 2, pp. 9–36 (1985).

*Matheson Gas Data Book*, Matheson Company, Inc. 1966.

Miller, D.L., "Ultrasonic Detection of Resonant Cavitation Bubbles in a Flow Tube by Their Second Harmonic Emissions", *Ultrasonics* Sep. 1981, 217–224.

STABILIZED HOMOGENOUS SUSPENSIONS AS COMPUTED TOMOGRAPHY CONTRAST AGENTS

CROSS-REFERENCE TO RELATED APPLICATIONS

This is a continuation-in-part of U.S. application Ser. No. 08/247,656, filed May 23, 1994, now abandoned. This application is related to Ser. No. 08/116,982, filed Sep. 7, 1993, now U.S. Pat. No. 5,456,900, issued Oct. 10, 1995, which is a division of U.S. application Ser. No. 07/980,594, filed Jan. 19, 1993, now U.S. Pat. No. 5,281,408, issued Jan. 25, 1994, which is a division of U.S. application Ser. No. 07/680,984, filed Apr. 5, 1991, now U.S. Pat. No. 5,205,290, issued Apr. 27, 1993.

The disclosures of each of the above applications are incorporated herein by reference in their entirety.

FIELD OF THE INVENTION

The present invention relates to suspensions for computed tomography. More particularly, the present invention relates to stabilized, substantially homogenous suspensions as contrast agents for computed tomography.

BACKGROUND OF THE INVENTION

Computed tomography (CT) is a commonly used diagnostic technique for the diagnosis of various diseases and maladies of the body, including abdominal and pelvic diseases. In 1978 alone, about 7.8 million body CT scans were performed.

CT imaging involves measuring the radiodensity of matter. Radiodensity is typically expressed in Hounsefield Units (HU). Hounsefield Units are a measure of the relative absorption of computed tomography X-rays by matter and is directly proportional to electron density. Water has been arbitrarily assigned a value of 0 HU, air a value of −1000 HU, and dense cortical bone a value of 1000 HU.

Various tissues in the body possess similar densities. This has caused difficulty in the generation of visual images by CT of tissues that possess similar densities and which are proximate each other. For example, it is difficult to generate separate CT images of the gastrointestinal (GI) tract and adjacent structures, including, for example, the blood vessels and the lymph nodes. Accordingly, contrast agents have been developed in an attempt to change the relative densities of different tissues, and thereby improve the diagnostic efficacy of CT. CT contrast agents are used in a majority of the CT imaging scans. For example, of the 7.8 million body CT scans performed in 1978, 6.6 million involved the use of intravenous contrast agents for the enhancement of vascular and/or visceral images.

Traditional CT contrast agents for imaging the gastrointestinal (GI) tract are generally based on radiodense, non-absorbable, heavy metal materials. Such materials assist in imaging the bowel by absorbing X-ray transmissions which increases the radiodensity of the bowel lumen. Common among such contrast agents are barium and iodinated compounds, including, for example, barium sulfate. Barium sulfate and iodinated compounds have been used for imaging the GI tract for the past 60 years and are widely used today for enhancing CT images of the upper and lower GI tract. They generally increase electron density in certain regions of the body, and are therefore classified as a "positive contrast agents."

Despite their widespread use, barium and iodinated compounds suffer from various drawbacks. For example, they are generally incompatible with other and/or newer imaging techniques, including vascular imaging techniques. This incompatibility is observed, for example, in CT angiography (CTA). In CTA, iodinated contrast agents are injected intravenously and images are obtained during the bolus phase of contrast. Highly detailed images of the vasculature are generally obtained using CTA by reformatting the axial images to yield a composite picture of the vessels. During this reformatting, the picture of the vasculature is optimized based on the measured density in the vessels being visualized. To perform this imaging, various baseline image subtractions are performed. However, the vascular image optimization becomes distorted and obscured in the presence in the bowel of radiodense contrast agents, for example, iodinated compounds. Consequently, difficulty is encountered in performing CTA and CT in the GI tract concurrently if any positive contrast agents, such as barium and iodinated compounds, are present.

Moreover, the viability of currently available CT contrast agents is generally extremely sensitive to concentration. If the concentration is too low, little contrast is observed. If the concentration is too high, beam hardening artifacts result and are observed as streaks in the resulting CT images. In addition, difficulty is typically encountered in visualizing the bowel mucosa with the currently available contrast agents.

Accordingly, new and/or better contrast agents for CT are needed. The present invention is directed to this, as well as other, important ends.

SUMMARY OF THE INVENTION

The present invention is directed to stabilized, substantially homogenous suspensions. Specifically, in one aspect, there is provided a stabilized, substantially homogenous suspension of a gas. The suspension has a negative density of about −40 Hounsefield units (HU) or less. In preferred form, the suspension comprises stabilized microspheres. The suspension may additionally comprise, as desired, a stabilizing material, thickening agent and/or a dispersing agent.

Another aspect of the invention relates to a stabilized, homogenous suspension of a gaseous precursor. In preferred form, the suspension comprises stabilized microspheres. The suspension may additionally comprise, as desired, a stabilizing material, thickening agent and/or a dispersing agent.

Yet another aspect of the invention relates to a contrast medium for computed tomography. The contrast agent comprises a stabilized, substantially homogenous suspension of a gas. At least a portion of the gas is derived from a gaseous precursor. In preferred form, the suspension comprises stabilized microspheres.

Still another aspect of the invention relates to a method for preparing a stabilized, substantially homogenous suspension of a gaseous precursor. The method comprises agitating an aqueous suspension of a stabilizing material in the presence of a gaseous precursor. In preferred form, the agitation comprises shaking or vortexing.

Yet another aspect of the invention relates to a method for preparing a stabilized, substantially homogenous suspension of a gas for use as a computed tomography contrast medium. The method comprises agitating an aqueous suspension of a stabilizing material in the presence of a gaseous precursor. The method further comprises activating the gaseous precursor. In preferred form, agitation of the aqueous suspension comprises shaking or vortexing. Also in preferred form, activation of the gaseous precursor involves a phase transition of a liquid gaseous precursor to a gas in vivo.

Still another aspect of the invention relates to a method of providing an image of an internal region of a patient. The method comprises administering to the patient a suspension as described above. The method also comprises scanning the patient using computed tomography to obtain visible images of the region.

Another aspect of the invention also relates to a method of providing an image of an internal region of a patient. The method comprises administering to the patient a stabilized, substantially homogenous suspension of a gaseous precursor. The gaseous precursor is allowed to undergo a phase transition from a liquid to a gas in vivo and the patient is scanned using computed tomography to obtain visible images of any diseased tissue in the patient.

The invention also relates to a method for diagnosing the presence of diseased tissue in a patient. The method comprises administering to the patient a suspension as described above. The method further comprises scanning the patient using computed tomography to obtain visible images of any diseased tissue in the patient.

Another aspect of the invention also relates to a method for diagnosing the presence of diseased tissue in a patient. The method comprises administering to the patient a stabilized, substantially homogenous suspension of a gaseous precursor. The gaseous precursor is allowed to undergo a phase transition from a liquid to a gas in vivo and the patient is scanned using computed tomography to obtain visible images of any diseased tissue in the patient.

Yet another aspect of the invention relates to a method for preparing in a patient a contrast medium for computed tomography. The method comprises administering to the patient a stabilized, substantially homogenous suspension of a gaseous precursor. The method further comprises allowing the gaseous precursor to undergo a phase transition from a liquid to a gas in vivo to provide the contrast medium.

These and other aspects of the invention will become more apparent from the present specification and claims.

DETAILED DESCRIPTION OF THE INVENTION

As employed above and throughout the disclosure, the following terms, unless otherwise indicated, shall be understood to have the following meanings.

"Suspension" refers to a mixture, dispersion or emulsion of finely divided colloidal particles floating in a liquid. The particles may be solid, liquid or gaseous.

"Emulsion" refers to a mixture of two or more liquids and is generally in the form of a colloidal mixture.

"Stabilized" refers to suspensions which have been formulated as a mixture of finely divided colloidal particles floating in a liquid with minimal aggregation. Preferably, the suspensions remain stabilized for a certain period of time. As discussed in detail below, certain preferred embodiments of the present invention involve suspensions of stabilized microspheres. In this context, the term "stabilized" refers to microspheres which are substantially resistant to degradation that is caused, for example, by the loss of structural or compositional integrity in the walls of the microspheres and/or by the loss of any significant portion of a gas or gaseous precursor encapsulated within the microsphere. As indicated above, the suspensions of the present invention are stable for a certain period of time. Preferably, the suspensions are stable for a period of time which permits use of the suspension, including, for example, use of the suspension for generating visible images of a region of a patient by computed tomography. Thus, the suspensions are preferably stable for a period of time to at least permit their administration to a patient and subsequent scanning of the patient with computed tomography.

"Stabilizing material" refers to a substance which is biocompatible and which is capable of stabilizing the present suspensions. Thus, with respect to suspensions which comprise, for example, finely divided liquid droplets and/or gaseous bubbles, the stabilizing materials are capable of minimizing aggregation of the droplets and/or bubbles. With respect to embodiments involving suspensions of microspheres, the stabilizing materials are capable of promoting the formation of the microspheres, as well as enhancing the resistance of the microspheres, once formed, to degradation caused, for example, by the loss of structural or compositional integrity in the walls of the microspheres and/or by the loss of any significant portion of a gas or gaseous precursor encapsulated therein. In preferred embodiments, the stabilizing materials impart the aforesaid properties to the suspensions for a certain period of time. Preferably, the stabilizing materials are capable of stabilizing suspensions for a period of time which permits use of the suspension, including, for example, in the generation of visible images of a region of a patient by computed tomography. Thus, the stabilizing materials are preferably capable of stabilizing the suspensions of the present invention for a period of time to at least permit their administration to a patient and subsequent scanning of the patient with computed tomography. In certain preferred embodiments, the stabilizing material comprises a surfactant. "Surfactant", as used herein, refers to a surface-active agent that is capable of altering (i) the surface tension of an aqueous solution; (ii) the surface tension between two liquids; and/or (iii) the surface tension between a liquid and a solid. Generally, alteration of the surface tension involves a reduction in surface tension. The surfactant may possess a net neutral, positive or negative charge. In certain preferred embodiments, the stabilizing material comprises a polymer. "Polymer", as used herein, refers to molecules formed from the chemical union of two or more repeating units. Accordingly, included within the term "polymer" are, for example, dimers, trimers and oligomers. The polymer may be synthetic, naturally-occurring or semisynthetic. In preferred form, the term "polymer" refers to molecules which comprise 10 or more repeating units. In certain other preferred embodiments, the stabilizing material comprises a non-polymeric material, including, for example, monomeric molecules.

"Dispersing agent" refers to a surface-active agent which, when added to a suspending medium of colloidal particles, including, for example, the suspensions, generally promotes uniform separation of particles. In certain preferred embodiments, the dispersing agent comprises a polymeric siloxane compound.

"Lipid" refers to a synthetic, semisynthetic or naturally-occurring amphipathic compound which comprises a hydrophilic component and a hydrophobic component. Lipids include, for example, fatty acids, neutral fats, phosphatides, glycolipids, aliphatic alcohols and waxes, terpenes and steroids.

"Alkyl" refers to an aliphatic hydrocarbon group which may be straight or branched having 1 to about 30 carbon atoms. "Lower alkyl" refers to an alkyl group having 1 to about 8 carbon atoms. "Higher alkyl" refers to an alkyl group having about 10 to about 30 carbon atoms. The alkyl group may be optionally substituted with one or more alkyl group substituents which may be the same or different, where "alkyl group substituent" includes, for example, halo, aryl, hydroxy, alkoxy, aryloxy, alkyloxy, alkylthio, arylthio, carboxy alkoxycarbonyl, oxo and cycloalkyl. There may be optionally inserted along the alkyl group one or more oxygen, sulphur or substituted nitrogen atoms, wherein the nitrogen substituent is lower alkyl. The alkyl group may be linear or branched. "Branched" refers to an alkyl group in which a lower alkyl group, such as methyl, ethyl or propyl, is attached to a linear alkyl chain. Exemplary alkyl groups include, for example, methyl, ethyl, i-propyl, n-butyl, t-butyl, n-pentyl, heptyl, octyl, nonyl, decyl, undecyl, dodecyl, tridecyl, tetradecyl, pentadecyl and hexadecyl. Preferred alkyl groups include the lower alkyl groups having 1 to about 4 carbon atoms and the higher alkyl groups having about 10 to about 16 carbon atoms.

"Microsphere" refers to a small spherical entity which is characterized by the presence of an internal void. Included among such entities are, for example, liposomes, micelles, bubbles, microbubbles, and the like. Preferred microspheres are formulated from the stabilizing materials described herein. As discussed in detail below, certain embodiments of the invention involve suspensions which comprise lipids. In microspheres formulated from these suspensions, the lipids may be in the form of a monolayer or bilayer, and the mono- or bilayer lipids may be used to form one or more mono- or bilayers. In the case of more than one mono- or bilayer, the mono- or bilayers are generally concentric. Thus, the lipids may be used to form a unilamellar microsphere (comprised of one monolayer or bilayer), an oligolamellar microsphere (comprised of about two or about three monolayers or bilayers) or a multilamellar microsphere (comprised of more than about three monolayers or bilayers). The internal void of the microspheres may contain a liquid, including, for example, an aqueous liquid, a gas, a gaseous precursor, and/or a solid or solute material, as desired.

"Gas filled microspheres" refers to microspheres in which there is encapsulated a gas. "Gaseous precursor filled microspheres" refers to microspheres in which there is encapsulated a gaseous precursor. The microspheres may be minimally, partially or substantially completely filled with the gas and/or gaseous precursor. In preferred embodiments, the microspheres are substantially completely filled with the gas and/or gaseous precursor.

"Thickening agent" refers to any of a variety of generally hydrophilic materials which, when incorporated in the present suspensions, act as viscosity modifying agents, emulsifying and/or solubilizing agents, suspending agents, and tonicity raising agents. It is contemplated that the thickening agents are capable of aiding in maintaining the stability of the suspensions due to such properties.

"Liposome" refers to a generally spherical cluster or aggregate of amphipathic compounds, including lipid compounds, typically in the form of one or more concentric layers, for example, bilayers. They may also be referred to herein as lipid microspheres.

"Semi-synthetic polymer" refers to a naturally-occurring polymer that has been chemically modified. Exemplary naturally-occurring polymers include, for example, polysaccharides.

"Biocompatible" refers to materials which are generally not injurious to biological functions and which will not result in any degree of unacceptable toxicity, including allergenic responses and disease states.

"Patient" refers to animals, including mammals, preferably humans.

The present invention is directed, in part, to stabilized, substantially homogenous suspensions. In a preferred embodiment, there is provided a stabilized, substantially homogenous suspension of a gas. The suspensions are characterized by having a negative density. This negative density makes the suspensions of the present invention particularly suitable for use as contrast agents for computed tomography (CT). Preferably, the suspensions have a negative density of about −40 Hounsefield units (HU) or less. In more preferred embodiments, the suspensions have a negative density of about −50 HU or less, such as about −60 HU, −70 HU, −80 HU and −90 HU, with negative densities of about −100 HU or less, such as about −110 HU, −120 HU, −130 HU, −140 HU, −150 HU, −160 HU, −170 HU, −180 HU and −190 HU, being even more preferred. Still more preferably, the suspensions have a negative density of about −200 HU or less, such as about −210 HU, −220 HU, −230 HU, −240 HU, −250 HU, −260 HU, −270 HU, −280 HU and −290 HU, and even more preferably, about −300 HU or less, such as about −310 HU, −320 HU, −330 HU, −340 HU, −350 HU, −360 HU, −370 HU, −380 HU and −390 HU. Suspensions having a negative density of about −400 HU or less, such as about −410 HU, −420 HU, −430 HU, −440 HU, −450 HU, −460 HU, −470 HU, −480 HU and −490 HU are still more preferred, with negative densities of about −500 HU or less being yet more preferred.

The suspensions of the present invention possess highly desirable stability properties. Indeed, a surprising and unexpected advantage of the present invention is that suspensions can be formulated, as described herein, which remain stable for a certain period of time. As described above, the present suspensions are preferably stable for at least a period of time which permits the generation of visible images, for example, CT images, of a region of a patient. Another surprising and unexpected advantage of the invention is that the suspensions generally lack a measure of stability that is associated with various of the prior art contrast agents. For example, Quay, International Application No. WO 94/16739 discloses contrast agents for ultrasound which are disclosed as having a stability of from about 5 days to about 1 year. Such high stability has certain advantages, including, for example, long shelf lives, which help to eliminate the need to repeatedly prepare fresh contrast agent. However, contrast agents which remain stable for such extended periods of time suffer from serious drawbacks in that difficulty can be experienced in connection with their metabolism and excretion from the body. Such stable contrast agents can accumulate in the body of the patient, particularly in fatty tissue and the liver. This is of particular concern inasmuch as the health effects from long term exposure to such contrast agents is unknown.

In addition to their excellent efficacy as contrast agents for computed tomography, the present suspensions generally remain stable throughout their useful life, and not generally significantly beyond that time frame, typically for a period of time which at least permits their administration to, and scanning of, a patient to generate visible images, for example, by CT. Thus, the suspensions of the present invention are stable for at least about several minutes. If desired, the suspensions can be formulated to be stable for periods longer than several minutes. For example, suspensions which are stable for several hours or about a day can be formulated according to the methods described herein. If desired, suspensions can be formulated which are stable for up to several days. As is apparent to one of ordinary skill in the art, based on the present disclosure, the length of time that any particular suspension is stable depends on various factors, including, for example, the components of the suspension, the method used to prepare the suspension, the environment to which the suspension is exposed after formulation, and the like. Depending on these various factors, the suspensions of the present invention will begin to separate and lose their homogeneity after about several minutes to about several days. Thus, the suspensions remain stable for a period of time which permits their administration to a patient and the patient to be scanned with, for example, CT. It is contemplated that the suspensions of the present invention generally do not remain stable significantly after the use thereof. For example, it is contemplated that they generally do not remain stable for a period of time substantially beyond that required for their administration to, and scanning of, a patient. Thus, the suspensions of the present invention can be readily metabolized by a patient, without danger of accumulation in fat tissue or the organs.

Moreover, it has been surprisingly and unexpectedly found that homogeneity of the suspensions can be restored conveniently with minimal effort. Homogeneity is important for uniformly accurate computed tomography scanning and can be easily restored by merely agitating the suspension. Such agitation can take the form of, for example, shaking the suspension. Techniques for agitating the suspensions is described in detail below in connection with methods for the preparation of the present suspensions. After agitation and resuspension, the suspension will remain stable for a period of time of from several minutes to several days, as described hereinbefore. Accordingly, the suspensions of the present invention possess potentially indefinite shelf lives, since resuspension of a separated and/or otherwise non-homogenous mixture is readily achieved.

Gases and Gaseous Precursors

In one aspect of the present invention, the suspensions comprise a gas. Preferred gases are gases which are extremely stable. The term stable gas, as used herein, refers to gases which are substantially inert and which are biocompatible. Preferred also are gases which have low solubility and/or diffusibility in aqueous media. In addition, preferred gases are those which provide the present suspensions with a desirable negative density, including a negative density of about −40 HU or less, as described above. Gases, such as perfluorocarbons, are especially preferred since they are less diffusible and are relatively insoluble in aqueous media.

Exemplary gases which may be incorporated in the present compositions include those selected from the group consisting of air, noble gases, such as helium, neon, argon and xenon, carbon dioxide, nitrogen, fluorine, oxygen, sulfur-based gases, such as sulfur hexafluoride and sulfur tetra fluoride, fluorocarbons, perfluorocarbon gases, and mixtures thereof. As noted above, perfluorocarbons are preferred gases. Exemplary perfluorocarbon gases include, for example, perfluoromethane, perfluoroethane, perfluoropropane, perfluorobutane, perfluorocyclobutane and mixtures thereof. It is contemplated that mixtures of different types of gases, such as mixtures of a perfluorocarbon gas and another type of gas, such as air, can also be used in the suspensions of the present invention. The gases discussed in Quay, International Application WO 93/05819, including the high "Q" factor gases described therein, may be used also. The disclosures of Quay, International Application WO 93/05819 are incorporated herein by reference in their entirety. In addition, paramagnetic gases and gases of isotopes, such as $^{17}O$, may be used. It is contemplated that suspensions which comprise these latter gases may also be used as contrast agents in connection with diagnostic techniques in addition to computed tomography, such as magnetic resonance imaging (MRI).

Other gases, including the gases exemplified above, would be readily apparent to one skilled in the art based on the present disclosure.

In particularly preferred embodiments of the present invention, the suspensions comprise microspheres. The microspheres are essentially bubbles of very small diameter comprising a "skin" or "envelope" that surrounds or encloses a cavity or void filled with liquid or a gas. Microspheres are particularly preferred in connection with gases that are derived from gaseous precursors, which are also preferred in the context of the present invention.

Gaseous precursors include materials that are capable of being converted in vivo to a gas. Exemplary precursors are materials which are liquids at room temperature and which, after being administered to a patient, undergo a phase transition to a gas in vivo. Preferably, the gaseous precursor is biocompatible, and the gas produced in vivo is biocompatible also. In addition, preferred gaseous precursors are materials which, when converted to a gas, provide the suspensions with a desirable negative density, including a negative density of about −40 HU or less, as described above in connection with the gases. Exemplary of suitable gaseous precursors are the perfluorocarbons. As the artisan will appreciate, a particular perfluorocarbon may exist in the liquid state when the suspensions are first made, and are thus used as a gaseous precursor. Alternatively, the perfluorocarbon may be used directly as a gas. Whether the perfluorocarbon is used as a liquid or a gas generally depends on its liquid/gas phase transition temperature, or boiling point. For example, a preferred perfluorocarbon, perfluoropentane, has a liquid/gas phase transition temperature (boiling point) of 29.5° C. This means that perfluoropentane will be a liquid at room temperature (about 25° C.), but will become a gas within the human body, the normal temperature of which is 37° C., which is above the transition temperature of perfluoropentane. Thus, under normal circumstances, perfluoropentane is a gaseous precursor. As a further example, there are the homologs of perfluoropentane, namely perfluorobutane and perfluorohexane. The liquid/gas transition of perfluorobutane is 4° C. and that of perfluorohexane is 57° C. Thus, perfluorobutane is potentially useful as a gaseous precursor, although more likely as a gas, whereas perfluorohexane would likely be useful as a gaseous precursor only because of its relatively high boiling point.

A wide variety of materials can be used as gaseous precursors in the present compositions. It is only required that the material be capable of undergoing a phase transition to the gas phase upon passing through the appropriate temperature. Suitable gaseous precursors include, for example, hexafluoroacetone, isopropyl acetylene, allene, tetrafluoroallene, boron trifluoride, 1,2-butadiene, 2,3-butadiene, 1,3-butadiene, 1,2,3-trichloro-2-fluoro-1,3-butadiene, 2-methyl-1,3-butadiene, hexafluoro-1,3-butadiene, butadiyne, 1-fluorobutane, 2-methylbutane, perfluorobutane, 1-butene, 2-butene, 2-methyl-1-butene, 3-methyl-1-butene, perfluoro-1-butene, perfluoro-2-butene, 4-phenyl-3-butene-2-one, 2-methyl-1-butene-3-yne, butyl nitrate, 1-butyne, 2-butyne, 2-chloro-1,1,1,4,4,4-hexafluorobutyne, 3-methyl-1-butyne, perfluoro-2-butyne, 2-bromo-butyraldehyde, carbonyl sulfide, crotononitrile, cyclobutane, methyl-cyclobutane, octafluorocyclobutane, perfluorocyclobutene, 3-chlorocyclopentene, perfluorocyclopentane, octafluorocyclopentene, cyclopropane, perfluorocyclopropane, 1,2-dimethylcyclopropane, 1,1-dimethylcyclopropane, 1,2-dimethylcyclopropane, ethylcyclopropane, methylcyclopropane, diacetylene, 3-ethyl-3-methyl diaziridine, 1,1,1-trifluorodiazoethane, dimethyl amine, hexafluorodimethylamine, dimethylethylamine, bis-(dimethylphosphine)amine, perfluorohexane, perfluoroheptane, perfluorooctane, 2,3-dimethyl-2-norbornane, perfluorodimethylamine, dimethyloxonium chloride, 1,3-dioxolane-2-one, 4-methyl-1,1,1,2-tetrafluoroethane, 1,1,1-trifluoroethane, 1,1,2,2-tetrafluoroethane, 1,1,2-trichloro-1,2,2-trifluoroethane, 1,1-dichloroethane, 1,1-dichloro-1,2,2,2-tetrafluoroethane, 1,2-difluoroethane, 1-chloro-1,1,2,2,2-pentafluoroethane, 2-chloro-1,1-difluoroethane, 1,1-dichloro-2-fluoroethane, 1-chloro-1,1,2,2-tetrafluoroethane, 2-chloro-1,1-difluoroethane, chloroethane, chloropentafluoroethane, dichlorotrifluoroethane, fluoroethane, perfluoroethane, nitropentafluoroethane, nitrosopentafluoroethane, perfluoroethylamine, ethyl vinyl ether, 1,1-dichloroethane, 1,1-dichloro-1,2-difluoroethane, 1,2-difluoroethane, methane, trifluoromethanesulfonylchloride, trifluoromethanesulfonylfluoride, bromodifluoronitrosomethane, bromofluoromethane, bromochlorofluoromethane, bromotrifluoromethane, chlorodifluoronltromethane, chlorodinitromethane, chlorofluoromethane, chlorotrifluoromethane, chlorodifluoromethane, dibromodifluoromethane, dichlorodifluoromethane, dichlorofluoromethane, difluoromethane, difluoroiodomethane, disilanomethane, fluoromethane, iodomethane, iodotrifluoromethane, nitrotrifluoromethane, nitrosotrifluoromethane, tetrafluoromethane, trichlorofluoromethane, trifluoromethane, 2-methylbutane, methyl ether, methyl isopropyl ether, methyllactate, methylnitrite, methylsulfide, methyl vinyl ether, neopentane, nitrous oxide, 1,2,3-nonadecane-tricarboxylic acid-2-hydroxytrimethylester, 1-nonene-3-yne, 1,4-pentadiene, n-pentane, perfluoropentane, 4-amino-4-methylpentan-2-one, 1-pentene, 2-pentene (cis), 2-pentene (trans), 3-bromopent-1-ene, perfluoropent-1-ene, tetrachlorophthalic acid, 2,3,6-trimethylpiperidine, propane, 1,1,1,2,2,3-hexafluoropropane, 1,2-epoxypropane, 2,2-difluoropropane, 2-aminopropane, 2-chloropropane, heptafluoro-1-nitropropane, heptafluoro-1-nitrosopropane, perfluoropropane, propene, hexafluoropropane, 1,1,1,2,3,3-hexafluoro-2,3-dichloropropane, 1-chloropropane, chloropropane-(trans), 2-chloropropane, 3-fluoropropane, propyne, 3,3,3-trifluoropropyne, 3-fluorostyrene, sulfur (di)-decafluoride ($S_2F_{10}$), 2,4-diaminotoluene, trifluoroacetonitrile, trifluoromethyl peroxide, trifluoromethyl sulfide, tungsten hexafluoride, vinyl acetylene and vinyl ether.

Perfluorocarbons are both preferred gases and preferred gaseous precursors for use in the suspensions of the present invention. Preferably, the perfluorocarbon has from about 1 carbon atom (4 fluorine atoms) to about 9 carbon atoms (20 fluorine atoms). Exemplary of perfluorocarbons of 1 to about 9 carbons are perfluorocarbons selected from the group consisting of perfluoromethane, perfluoroethane, perfluoropropane, perfluorobutane, perfluorocyclobutane, perfluoropentane, perfluorohexane, perfluoroheptane, perfluorooctane and perfluorononane. Preferably, the perfluorocarbon is selected from the group consisting of perfluoropentane, perfluorohexane and perfluorooctane, with perfluoropentane being particularly preferred.

In certain preferred embodiments, a gas, for example, air or a perfluorocarbon gas, is combined with a liquid perfluorocarbon, such as perfluorooctylbromide (PFOB), perfluorodecalin, perfluorododecalin, perfluorooctyliodide, perfluorotripropylamine, and perfluorotributylamine.

As noted above, certain preferred embodiments of the present invention involve suspensions which comprise microspheres. The size of the microspheres can be adjusted, if desired, by a variety of procedures including, for example, microemulsification, vortexing, extrusion, filtration, sonication, homogenization, repeated cycles of freezing and thawing, extrusion under pressure through pores of defined size, and similar methods.

For intravascular use, the microspheres preferably have diameters of less than about 30 μm, and more preferably, less than about 12 μm. For targeted intravascular use including, for example, binding to certain tissue, such as cancerous tissue, the microspheres can be significantly smaller, for example, less than 100 nm in diameter. For enteric or gastrointestinal use, the microspheres can be significantly larger, for example, up to a millimeter in size. Preferably, the microspheres are sized to have diameters between about 20 μm and 100 μm.

Tabulated below is a listing of a series of gaseous precursors which undergo phase transitions from liquid to gas at relatively close to normal human body temperature (37° C.) or below. Also listed in the table are the sizes, in diameter, of emulsified droplets that would be required to form a microsphere of a maximum size of about 10 μm.

TABLE 1

Physical Characteristics of Gaseous Precursors and Diameter of Emulsified Droplet to Form a 10 μm Microsphere

| Compound | Molecular Weight | Boiling Point (°C.) | Density | Diameter (μm) of emulsified droplet to make 10 micron microsphere |
|---|---|---|---|---|
| perfluoropentane | 288.04 | 29.5 | 1.7326 | 2.9 |
| 1-fluorobutane | 76.11 | 32.5 | 6.7789 | 1.2 |
| 2-methyl-butane (isopentane) | 72.15 | 27.8 | 0.6201 | 2.6 |
| 2-methyl-1-butene | 70.13 | 31.2 | 0.6504 | 2.5 |
| 2-methyl-2-butene | 70.13 | 38.6 | 0.6623 | 2.5 |
| 1-butene-3-yne-2-methyl | 66.10 | 34.0 | 0.6801 | 2.4 |
| 3-methyl-1-butyne | 68.12 | 29.5 | 0.6660 | 2.5 |
| octafluorocyclobutane | 200.04 | −5.8 | 1.48 | 2.8 |
| decafluorobutane | 238.04 | −2 | 1.517 | 3.0 |
| hexafluoroethane | 138.01 | −78.1 | 1.607 | 2.7 |

*Source: Chemical Rubber Company Handbook of Chemistry and Physics Robert C. Weast and David R. Lide, eds. CRC Press, Inc. Boca Raton, Florida. (1989–1990).

It is an aspect of the present invention to optimize the utility of the suspensions, including suspensions which comprise microspheres, by using gases of limited solubility. Limited solubility, as used herein, refers to the ability of the gas to diffuse, for example, out of microspheres by virtue of its solubility in the surrounding aqueous medium. A greater solubility in the aqueous medium imposes a gradient with the gas in the microsphere such that the gas will have a tendency to diffuse out of the microsphere. A lesser solubility in the aqueous medium will decrease the gradient between the microsphere and the interface such that the diffusion of the gas out of the microsphere will be impeded. Preferably, the gas entrapped in the microsphere has a solubility less than that of oxygen, namely, 1 part gas in 32 parts water. See *Matheson Gas Data Book*, Matheson Company, Inc. (1966). More preferably, the gas entrapped in the microsphere possesses a solubility in water less than that of air; and even more preferably, the gas entrapped in the microsphere possesses a solubility in water less than that of nitrogen.

The amount of gas and/or gaseous precursor which is incorporated in the present suspensions can vary, and depends upon various factors, including, for example, the particular stabilizing materials, thickening agents, dispersing agents, and the like, which, if desired, are employed in the suspensions. It is preferred that the concentration of gas or gaseous precursor is at least sufficient to impart desirable properties to the suspensions including, for example, a desirable negative density when used as contrast agents. In preferred embodiments, which involve a gaseous precursor, as well as a combination of gaseous precursors, the total concentration of gaseous precursor is from about 0.1 wt. % to about 5 wt. %. More preferably, the total concentration of gaseous precursor is from about 0.5 wt. % to about 2 wt. %, with a total concentration of about 1 wt. % being even more preferred.

Stabilizing Materials

In certain preferred embodiments of the present invention, the suspensions further comprise a stabilizing material. It has been surprisingly and unexpectedly found that the stabilizing materials, as defined herein, are capable of promoting the formation of substantially homogenous suspensions. It has also been surprisingly and unexpectedly found that the stabilizing materials, as defined herein, are capable of promoting the formation of microspheres, as well as enhancing the resistance of microspheres, once formed, to degradation caused by, for example, the loss of structural or compositional integrity in the walls of the microspheres and/or by the loss of any significant portion of a gas or gaseous precursor which may be encapsulated within the microsphere.

A wide variety of substances are available which can be used as stabilizing materials in the suspensions of the present invention. Preferred stabilizing materials are substances that are biocompatible. Preferred also are substances which are capable of raising the viscosity of the suspensions. It has been found that surface-active agents, including, for example, surfactants, are particularly suitable for use as stabilizing materials in the suspensions of the present invention. In preferred embodiments, the surfactants are selected from the group consisting of anionic, cationic, zwitterionic and nonionic surfactants. Preferred among these surfactants are the nonionic surfactants.

Exemplary nonionic surfactants include, for example, polyoxyethylenepolyoxypropylene glycol block copolymers, sorbitan fatty acid esters and fluorine-containing surfactants. Preferred among the polyoxyethylene-polyoxypropylene glycol block copolymers are α-hydroxy-ω-hydroxypoly(oxyethylene)-poly(oxypropylene)poly(oxyethylene) block copolymers. These latter block copolymers are generally referred to as poloxamer copolymers. Examples of poloxamer copolymers which are particularly suitable for use in the present suspensions include, for example, poloxamer F68, poloxamer L61 and poloxamer L64. These poloxamer copolymers are commercially available from Spectrum 1100 (Houston, Tex.).

Preferred among the sorbitan fatty acid esters are, for example, poly(oxy-1,2-ethanediyl) derivatives of higher alkyl esters of sorbitan. Examples of such esters of sorbitan include, for example, sorbitan monolaurate, sorbitan monooleate, sorbitan monopalmitate and sorbitan monostearate. These, as well as other derivatives of sorbitan, are typically referred to as polysorbates, including, for example, polysorbate 20, polysorbate 40, polysorbate 60 and polysorbate 80. Various of the polysorbates are commercially available from Spectrum 1100 (Houston, Tex.).

The fluorine-containing surfactants include surfactants containing one or more fluorine atoms. Exemplary of such surfactants include those commercially available from DuPont Chemicals (Wilmington, Del.) and which are sold under the tradename Zonyl™, including, for example, Zonyl™ FSN-100 and Zonyl™ FSO-100.

As noted above, ionic surfactants, for example, anionic and cationic surfactants, may be used as stabilizing materials in the present suspensions. Exemplary of suitable anionic surfactants is sodium lauryl sulfate, commercially available from Witco Corp. (New York, N.Y.). Suitable cationic surfactants include ammonium salts, particularly ammonium salts substituted with higher alkyl groups. Included among such ammonium salts are lauryltrimethylammonium bromide, cetyltrimethylammonium bromide, myristyltrimethylammonium bromide, alkyldimethylbenzylammonium chloride (where alkyl is, for example, $C_{12}$, $C_{14}$ or $C_{16}$), benzyldimethyldodecylammonium bromide/chloride, benzyldimethylhexadecylammonium bromide/chloride, benzyldimethyltetradecylammonium bromide/chloride, cetyldimethylethylammonium bromide/chloride, and cetylpyridinium bromide/chloride. In addition, the cationic surfactant can comprise a cationic lipid, including for example, N-[1-(2,3-dioleoyloxy)propyl]-N,N,N-trimethylammonium chloride (DOTMA), 1,2-dioleoyloxy-3-(trimethylammonio)propane (DOTAP), 1,2-dioleoyl-e-(4'-trimethylammonio)butanoyl-sn-glycerol (DOTB) and lipids bearing cationic polymers, such as polylysine and polyarginine.

Other surfactants, including those exemplified above, would be apparent to one of ordinary skill in the art based on the present disclosure.

As indicated above, suspensions in which there is incorporated a stabilizing material represent a preferred embodiment of the present invention. It is contemplated that the suspensions can comprise a mixture of stabilizing materials.

The concentration of each stabilizing material, when present in the suspensions of the present invention, can vary and depends upon various factors, including, for example, the particular stabilizing material(s), gases, gaseous precursors, and the like, employed. It is preferred that the total concentration of stabilizing material is at least sufficient to cause stabilization of the suspension. If the suspension comprises microspheres, it is preferred that the total concentration of stabilizing material is at least sufficient to promote formation of the microspheres as well as subsequent stabilization thereof. In preferred embodiments, the concentration of each stabilizing material is from about 10 ppm to about 1,000 ppm. More preferably, the concentration of each stabilizing material is from about 50 ppm to about 750 ppm, with concentrations of about 100 ppm to about 500 ppm being even more preferred.

Thickening Agents

In certain preferred embodiments of the present invention, the suspensions further comprise a thickening agent. If desired, two or more thickening agents can be employed in the present suspensions. Suitable thickening agents for use in the present suspensions include starches, gums, pectin, casein, gelatin and phycocolloids, including carrageenan, algin and agar; semi-synthetic cellulose derivatives; polyvinyl alcohol and carboxyvinylates; and bentonite, silicates and colloidal silica. Exemplary of the foregoing materials are, for example, carbohydrates and the phosphorylated and sulfonated derivatives thereof; agarose; polyethers, including polyethers having a molecular weight of, for example, from about 400 to about 100,000; di- and trihydroxy alkanes and their polymers having a molecular weight of, for example, about 200 to about 50,000; acacia; diethanolamine; glycerol monostearate; lanolin alcohols; lecithin; mono- and diglycerides; monoethanolamine; oleic acid; oleyl alcohol;

polyoxyethylene 50 stearate; polyoxyl 35 castor oil; polyoxyl 10 oleyl ether; polyoxyl 20 cetostearyl ether; polyoxyl 40 stearate; propylene glycol diacetate; propylene glycol monostearate; sodium stearate; stearic acid; trolamine; emulsifying wax; agar; alginic acid; aluminum monostearate; bentonite; magma; carbomer 934P; hydroxyethyl starch; carboxymethylcellulose; calcium and sodium and sodium 12; carrageenan; cellulose; dextran; gelatin; guar gum; locust bean gum; veegum; hydroxyethyl cellulose; hydroxypropylmethylcellulose; magnesium-aluminum-silicate; methylcellulose; pectin; polyethylene oxide; povidone; propylene glycol alginate; silicon dioxide; sodium alginate; tragacanth; xanthan gum; α-d-gluconolactone; glycerol; mannitol; polyethyleneglycol (PEG); polyvinylpyrrolidone (PVP); polyvinylalcohol (PVA); polypropylene glycol; polysorbate; sorbitol; propyleneglycol; and glycerol.

Preferred among the foregoing thickening agents are gums, including xanthan gum, cellulose derivatives, including methyl cellulose and carboxymethyl cellulose, and carrageenan. Particularly preferred among the thickening agents is methyl cellulose.

The concentration of thickening agent, when present in the suspensions of the present invention, can vary and depends upon various factors, including, for example, the particular thickening agent(s), gases, gaseous precursors, stabilizing materials, and the like, employed. It is preferred that the total concentration of thickening agent is at least sufficient to impart desirable properties to the suspensions, including, for example, stabilization of the suspensions. In preferred embodiments, the concentration of thickening agent is from about 0.1 wt. % to about 10 wt. %. More preferably, the concentration of thickening agent is from about 0.2 wt. % to about 7.5 wt. %, with concentrations of about 0.25 wt. % to about 5 wt. % being even more preferred. Still more preferably, the concentration of thickening agent is from about 0.3 wt. % to about 3 wt. %.

Dispersing Agents

The suspensions of the present invention also preferably comprise one or more dispersing agents. It is contemplated that the dispersing agents are also capable of contributing to the stability of the suspensions. In certain preferred embodiments, the dispersing agent comprises a polymeric siloxane compound. Preferably, the polymeric siloxane compound is substantially or completely alkylated with alkyl groups, with lower alkyl groups being preferred. More preferably, the polymeric siloxane compound is substantially or completely methylated. A particularly suitable polymeric siloxane compound for use as a dispersing agent in the suspensions of the present invention is α-(trimethylsilyl)-ω-methylpoly[oxy(dimethylsilylene)], which is also referred to as simethicone, and which is commercially available from Dow Corning (Midland, Mich.).

The amount of dispersing agent which is included in the suspensions can vary, and depends upon various factors, including, for example, the particular dispersant(s), stabilizing materials, thickening agents, gases, gaseous precursors, and the like, which, as desired, are employed in the suspensions. It is preferred that the concentration of dispersing agent is at least sufficient to impart desirable properties to the suspensions, including, for example, promoting desirable stabilization of the suspensions. In preferred embodiments, the concentration of dispersing agent is from about 10 ppm to about 1,000 ppm. More preferably, the concentration of dispersing agent is from about 50 ppm to about 750 ppm, with concentrations of from about 100 ppm to about 500 ppm being even more preferred.

Auxiliary Materials

In addition to the stabilizing materials, thickeners and dispersing agents discussed above, there exists a wide variety of auxiliary materials which, if desired, can be incorporated in the suspensions of the present invention. Depending upon, for example, the physical and/or chemical properties of the auxiliary materials, they may impart desirable properties to the suspensions. For example, it is contemplated that certain of the auxiliary materials are capable of contributing to the formation and/or stabilization of the present suspensions. In embodiments involving microspheres, the auxiliary materials may promote formation and/or stabilization of the microspheres. In addition, the auxiliary materials may enhance the functioning of the stabilizing materials of the present invention, or may contribute some desired property in addition to that afforded by the present stabilizing material. For example, it is contemplated that certain of the auxiliary materials can enhance the organoleptic properties of the suspensions.

As would be apparent to one of ordinary skill in the arts based on the teachings in the present disclosure, it is not always apparent whether a particular material, when incorporated in the present suspensions, acts as a stabilizing material, thickening agent or dispersing agent as described above, or whether it is acting as an auxiliary material, since the functioning of the substance in question is generally determined empirically, or by the results produced with respect to the formulation of a particular stabilized suspension. For example, the simple combination of a biocompatible lipid, which, as described more fully hereinafter, is generally an auxiliary material within the context of the present invention, and water or saline, when shaken, will often give a cloudy solution subsequent to autoclaving for sterilization. Such a cloudy solution may function as a contrast agent, but is aesthetically objectionable and may imply instability in the form of undissolved or undispersed lipid particles. Propylene glycol, which is identified herein as a thickening agent, may be added to remove this cloudiness by facilitating dispersion or dissolution of the lipid particles. However, it is contemplated that the propylene glycol may also function to improve formation of microspheres and stabilization by increasing the surface tension on the microsphere membrane or skin. It is possible also that the propylene glycol functions as an additional layer that coats the membrane or skin of a microsphere, thus providing additional stabilization.

Materials which function as stabilizing materials and/or as auxiliary materials for use in the preparation of stabilized suspensions would be apparent to one skilled in the art based on the present disclosure. Such materials include conventional surfactants which are disclosed, for example, in D'Arrigo, U.S. Pat. Nos. 4,684,479 and 5,215,680, the disclosures of which are incorporated herein by reference, in their entirety.

Additional auxiliary and/or stabilizing materials includes for example, oils, such as peanut oil, canola oil, olive oils safflower oil, corn oil, or any other oil which is commonly known to be ingestible. Another stabilizing/auxiliary material is trehalose.

As noted above, biocompatible lipids may be included in the suspensions of the present invention. Exemplary of such lipids include, for example, lysolipids, phospholipids, such as phosphatidylcholines with both saturated and unsaturated lipids, including dioleoylphosphatidylcholine, dimyristoylphosphatidylcholine, dipentadecanoylphosphatidylcholine, dilauroylphosphatidylcholine, dipalmitoylphosphatidylcholine (DPPC) and distearoylphosphatidylcholine (DSPC); phosphatidylethanolamines, such as dioleoylphosphatidylethanolamine, distearoylphosphatidylethanolamine and dipalmitoylphosphatidylethanolamine (DPPE); phosphatidylserines; phosphatidylglycerols; phosphatidylinositols; sphingolipids, such as sphingomyelin; glycolipids, such as ganglioside GM1 and GM2; glucolipids; sulfatides; glycosphingolipids; phosphatidic acid, such as dipalmitoylphosphatidic acid (DPPA); palmitic acid; stearic acid; arachidonic acid; oleic acid; lipids bearing polymers, including hydrophilic polymers, such as polyethyleneglycol, chitin, hyaluronic acid or polyvinylpyrrolidone, with preferred lipids bearing polymers including dipalmitoylphosphatidylethanolamine-PEG 5000 (DPPE-PEG 5000), which means a dipalmitoylphosphatidylethanolamine lipid having a PEG polymer of a mean average molecular weight of about 5000 attached thereto; lipids bearing sulfonated mono-, di-, oligo- or polysaccharides, such as arabinans, fructans, fucans, galactans, galacturonans, glucans, mannans, xylans (such as, for example, inulin), levan, fucoidan, carrageenan, galactocarolose, pectic acid, amylose, pullulan, glycogen, amylopectin, cellulose, dextran, pustulan, chitin, agarose, keratin, chondroitan, dermatan, hyaluronic acid, alginic acid, xanthan gum, starch and various other natural homopolymer or heteropolymers, including those containing one or more of the following aldoses, ketoses, acids or amines: erythrose, threose, ribose, arabinose, xylose, lyxose, allose, altrose, glucose, mannose, gulose, idose, galaclose, talose, erythrulose, ribulose, xylulose, psicose, fructose, sorbose, tagarose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof; cholesterols and cholesterol hemisuccinate; tocopherols and tocopherol hemisuccinate; lipids with ether and ester-linked fatty acids; polymerized lipids; diacetyl phosphate; dicetyl phosphate; stearylamine; cardiolipin; phospholipids with short chain fatty acids ($C_6$ to $C_8$); synthetic phospholipids with asymmetric acyl chains, for example, a first acyl chain of $C_6$ and a second acyl chain of $C_{12}$; ceramides; polyoxyethylene fatty acid esters, polyoxyethylene fatty alcohols, polyoxyethylene fatty alcohol ethers, glycerol polyethylene glycol oxystearate, glycerol polyethylene glycol ricinoleate, sterols, ethoxylated soybean sterols, ethoxylated castor oil, and polyoxyethylene fatty acid stearates; sterol aliphatic acid esters, including cholesterol sulfate, cholesterol butyrate, cholesterol isobutyrate, cholesterol palmirate, cholesterol stearate, lanosterol acetate, ergosterol palmitate, and phytosterol n-butyrate; sterol esters of sugar acids, including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols, including lauryl glucuronide, stearoyl glucuronide, myristoyl glucuronide, lauryl gluconate, myristoyl gluconate, and stearoyl gluconate; esters of sugars and aliphatic acids, including sucrose laurate, fructose laurate, sucrose palmirate, sucrose stearate, glucuronic acid, gluconic acid, accharic acid, and polyuronic acid; saponins, including sarsasapogenin, smilagenin, hederagenin, oleanolic acid, and digitoxigenin; glycerol dilaurate, glycerol trilaurate, glycerol dipalmitate, glycerol and glycerol esters, including glycerol tripalmitate, glycerol distearate, glycerol tristearate, glycerol dimyristate, glycerol trimyristate; long chain alcohols of, for example, about 10 to about 30 carbon atoms, including n-decyl alcohol, lauryl alcohol, myristyl alcohol, cetyl alcohol, and n-octadecyl alcohol; alkyl phosphonates, alkyl phosphinates and alkyl phosphites; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxy-1-thio-α-D-mannopyranoside; 12-(((7'-diethylaminocoumarin-3-yl)carbonyl)methylamino) octadecanoic acid; N-[12-(((7'-diethylaminocoumarin-3-yl)carbonyl)methylamino)octadecanoyl]-2-aminopalmitic acid; cholesteryl(4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine; palmitoylhomocysteine; saturated fatty acids, including, for example, lauric, myristic, palmitic and stearic acids; and unsaturated fatty acids, including, for example, isolauric, isomyristic, isopalmitic and isostearic acids; and/or combinations thereof.

In certain embodiments, the auxiliary materials preferably comprise a mixture of two or more lipids. An example of a preferred mixture of lipids is a mixture of DPPC, DPPA and DPPE-PEG-5000.

As discussed in detail below, a wide variety of methods are available for the preparation of the present suspensions, including suspensions comprising microspheres. Included among these methods are, for example, shaking, drying, gas-installation, spray drying, and the like. In embodiments which involve the use of a lipid as, for example, an auxiliary material, the suspensions are preferably prepared from lipids which remain in the gel state, this being the temperature at which a lipid bilayer converts from the gel state to the liquid crystalline state. See, e.g., Chapman et al., *J. Biol. Chem.* 1974 249, 2512-2521, the disclosures of which are hereby incorporated by reference herein, in their entirety. The following table lists representative lipids and their phase transition temperatures.

TABLE 2

| Saturated Diacyl-sn-Glycero-3-Phosphocholines: Main Chain Phase Transition Temperatures | |
|---|---|
| Carbons in Acyl Chains | Main Phase Transition Temperature °C. |
| 1,2-(12:0) | −1.0 |
| 1,2-(13:0) | 13.7 |
| 1,2-(14:0) | 23.5 |
| 1,2-(15:0) | 34.5 |
| 1,2-(16:0) | 41.4 |
| 1,2-(17:0) | 48.2 |
| 1,2-(18:0) | 55.1 |
| 1,2-(19:0) | 61.8 |
| 1,2-(20:0) | 64.5 |
| 1,2-(21:0) | 71.1 |
| 1,2-(22:0) | 74.0 |
| 1,2-(23:0) | 79.5 |
| 1,2-(24:0) | 80.1 |

See, e.g., Derek Marsh, CRC *Handbook of Lipid Bilayers*, p. 139 (CRC Press, Boca Raton, Fla. 1990).

Preferably, the suspensions of the present invention are formulated with one or more materials which possess relatively high water binding capacities. When used, for example, in the GI region, such materials can bind large amounts of free water. This enables the materials to carry a large volume of liquid through the GI tract, thereby filling and distending the tract. The filled and distended GI tract permits enhanced CT imaging of the region.

In addition, where imaging of the GI region is desired, the materials from which the suspensions are formulated are preferably not substantially degraded in, and absorbed from, the GI region. Thus, metabolism and absorption within the GI tract is preferably minimized to avoid removal of the contrast agent. This also avoids the possible formation of gas within the GI tract from such degradation. For imaging the GI region, preferred materials are capable of displacing air and minimizing the formation of large air bubbles within the contrast medium.

As noted above, it is often desirable to incorporate one or more auxiliary materials which are capable of enhancing the organoleptic properties of the suspensions. It is contemplated that various of these materials are capable also of acting as a stabilizing material, thickener and/or dispersant. Included among auxiliary materials which can improve the organoleptic properties of the suspensions are sweetening agents, for example, sucrose, fructose, lactose, saccharin, or aspartame, and flavoring agents, for example, peppermint, oil of wintergreen or cherry flavoring. Preferably, a sweetening agent is incorporated in the present suspensions, with fructose being a preferred sweetening agent.

The amount of organoleptic enhancing agent which is included in the suspensions can vary, and depends upon various factors, including, for example, the particular stabilizing materials, thickening agents, gases, gaseous precursors, dispersing agents, and the like, which, as desired, are employed in the suspensions. It is preferred that the concentration of organoleptic enhancing agent is at least sufficient to impart desirable properties to the suspensions, including, for example, improved taste. In preferred embodiments, the concentration of organoleptic enhancing agent is from about 0.1 wt. % to about 10 wt. %. More preferably, the concentration of organoleptic enhancing agent is from about 0.5 wt. % to about 5 wt. %, with concentrations of about 2 wt. % being even more preferred.

Aqueous Diluents

A desired component of the stabilized suspensions of the present invention is an aqueous environment, particularly with respect to suspensions comprising microspheres. Many of the stabilizing materials discussed above involve compounds which comprise both hydrophobic and hydrophilic properties. Accordingly, there can be a predisposition among the present suspensions to form microspheres, which are highly stable configurations in such an environment. The diluents which can be employed to create such an aqueous environment include, but are not limited to, water, either deionized or containing any number of dissolved salts which will not interfere with the creation and maintenance of the stabilized suspensions or their use as CT agents, and normal saline and physiological saline.

Methods of Preparation

The stabilized suspensions of the present invention may be prepared by a number of suitable methods. These are described below separately for suspensions which comprise a gas, a gaseous precursor, and suspensions comprising both a gas and a gaseous precursor.

Methods of Preparation Using a Gas

Suspensions comprising a gas can be prepared by agitating an aqueous solution containing, if desired, a stabilizing material, preferably a surfactant, in the presence of a gas. If a lipid is incorporated in the suspensions, the agitating is preferably conducted at a temperature below the gel to liquid crystalline phase transition temperature of the lipid. The term agitating, and variations thereof, as used herein, means any motion that shakes an aqueous solution such that gas is introduced from the local ambient environment into the aqueous solution. The shaking must be of sufficient force to result in the formation of a stabilized suspension, including stabilized suspensions of microspheres, and particularly gas filled microspheres. The shaking may be by swirling, such as by vortexing, side-to-side, or up and down motion. Different types of motion may be combined. Also, the shaking may occur by shaking the container holding the aqueous lipid solution, or by shaking the aqueous solution within the container without shaking the container itself.

Further, the shaking may occur manually or by machine. Mechanical shakers that may be used include, for example, a shaker table such as a VWR Scientific (Cerritos, Calif.) shaker table, or a Wig-L-Bug® Shaker from Dental Mfg. Ltd. (Lyons, Ill.), which has been found to give excellent results. It has been found that certain modes of shaking or vortexing can be used to make stable microspheres within a preferred size range. Shaking is preferred, and it is preferred that the shaking be carried out using the Wig-L-Bug® mechanical shaker. In accordance with this preferred method, it is preferred that a reciprocating motion be utilized to generate the stabilized suspensions, and particularly stabilized suspensions comprising microspheres. It is even more preferred that the motion be reciprocating in the form of an arc. It is still more preferred that the motion be reciprocating in the form of an arc between about 2° and about 20°, and yet further preferred that the arc be between about 5° and about 8°. It is most preferred that the motion is reciprocating between about 6° and about 7°, most particularly about 6.5°. It is contemplated that the rate of reciprocation, as well as the arc thereof, is particularly important in connection with the formation microspheres. Preferably, the number of reciprocations or full cycle oscillations, is from about 1000 to about 20,000 per minute. More preferably, the number of reciprocations or oscillations is from about 5000 to about 8000. The Wig-L-Bug®, referred to above, is a mechanical shaker which provides 2000 pestle strikes every 10 seconds, i.e., 6000 oscillations every minute. Of course, the number of oscillations is dependent upon the mass of the contents being agitated, with the larger the mass, the fewer the number of oscillations. Another means for producing shaking includes the action of gas emitted under high velocity or pressure.

It will also be understood that preferably, with a larger volume of aqueous solution, the total amount of force will be correspondingly increased. Vigorous shaking is defined as at least about 60 shaking motions per minute, and is preferred. Vortexing at about 60 to 300 revolutions per minute is more preferred. Vortexing at about 300 to 1800 revolutions per minute is even more preferred.

The formation of gas filled microspheres upon shaking can be detected visually. In addition to the simple shaking methods described above, more elaborate methods can also be employed. Such elaborate methods include, for example, liquid crystalline shaking gas instillation processes and vacuum drying gas instillation processes, such as those described in copending U.S. application Ser. No. 08/076, 250, filed Jun. 11, 1993, which is incorporated herein by reference, in its entirety. When such processes are used, the stabilized microspheres which are to be gas filled, may be prepared prior to gas installation using any one of a variety of conventional preparatory techniques, including conventional liposome preparatory techniques in connection with suspensions containing lipids, and which will be apparent to those skilled in the art. Among the preparatory techniques are freeze-thaw, as well as techniques such as sonication, chelate dialysis, homogenization, solvent infusion, microemulsification, spontaneous formation, solvent vaporization, French pressure cell technique, controlled detergent dialysis, and others, each involving preparing the microspheres in various fashions. See, e.g., Madden et al., *Chemistry and Physics of Lipids,* 1990 53, 37–46, the disclosures of which are hereby incorporated herein by reference in their entirety.

Gas filled microspheres prepared in accordance with the methods described herein can range in size from below a micron to over 100 µm. In addition, after extrusion and sterilization procedures, agitation or shaking provides suspensions of microspheres which, if prepared from suspensions comprising lipid, provides substantially no or minimal residual anhydrous lipid phase in the remainder of the solution. (Bangham, A. D., Standish, M. M, & Watkins, J. C. (1965) *J. Mol. Biol. Vol.* 13, pp. 238–252 (1965).

The size of gas filled microspheres can be adjusted, if desired, by a variety of procedures, including microemulsification, vortexing, extrusion, filtration, sonication, homogenization, repeated freezing and thawing cycles, extrusion under pressure through pores of defined size, and similar methods. It may also be desirable to use the microspheres of the present invention as they are formed, without any attempt at further modification of the size thereof.

The gas filled microspheres may be sized by a simple process of extrusion through filters; the filter pore sizes control the size distribution of the resulting gas filled microspheres. By using two or more cascaded or stacked set of filters, for example, a 10 µm filter followed by an 8 µm filter, the gas filled microspheres can be selected to have a very narrow size distribution around 7 to 9 µm. After filtration, these stabilized gas filled microspheres remain stable for over 24 hours.

The sizing or filtration step may be accomplished by the use of a filter assembly when the suspension is removed from a sterile vial prior to use, or more preferably, the filter assembly may be incorporated into the syringe itself during use. The method of sizing the microspheres will then comprise using a syringe comprising a barrel, at least one filter, and a needle; and will be carried out by a step of extracting which comprises extruding said microspheres from said barrel through said filter fitted to said syringe between said barrel and said needle, thereby sizing said microspheres before they are administered to a patient in the course of using the microspheres as CT contrast agents in accordance with the present invention. The step of extracting may also comprise drawing said microspheres into said syringe, where the filter will function in the same way to size the microspheres upon entrance into the syringe. Another alternative is to fill such a syringe with microspheres which have already been sized by some other means, in which case the filter now functions to ensure that only microspheres within the desired size range, or of the desired maximum size, are subsequently administered by extrusion from the syringe.

In preferred embodiments, the solution or suspension of microspheres is extruded through a filter and is heat sterilized prior to shaking. Once gas filled microspheres are formed, they may be filtered for sizing as described above. These steps prior to the formation of gas and gaseous precursor filled microspheres provide the advantages, for example, of reducing the amount of unhydrated stabilizing compound, and thus providing a significantly higher yield of gas filled microspheres, as well as and providing sterile gas filled microspheres ready for administration to a patient. For example, a mixing vessel such as a vial or syringe may be filled with a filtered stabilizing material, and the suspension may then be sterilized within the mixing vessel, for example, by autoclaving. Gas may be instilled into the suspension to form gas filled microspheres by shaking the sterile vessel. Preferably, the sterile vessel is equipped with a filter positioned such that the gas filled microspheres pass through the filter before contacting a patient.

The first step of this preferred method, extruding the solution of stabilizing compound through a filter, decreases the amount of unhydrated material by breaking up any dried materials and exposing a greater surface area for hydration. Preferably, the filter has a pore size of about 0.1 to about 5 µm, more preferably, about 0.1 to about 4 µm, even more preferably, about 0.1 to about 2 µm, and still more preferably, about 1 µm. Unhydrated compound, appears as amorphous clumps of non-uniform size and is undesirable.

The second step, sterilization, provides a composition that may be readily administered to a patient for CT imaging. Preferably, sterilization is accomplished by heat sterilization, preferably, by autoclaving the solution at a temperature of at least about 100° C., and more preferably, by autoclaving at about 100° C. to about 130° C., even more preferably, about 110° C. to about 130° C., still more preferably, about 120° C. to about 130° C., and even more preferably, about 130° C. Preferably, heating occurs for at least about 1 minute, more preferably, about 1 to about 30 minutes, even more preferably, about 10 to about 20 minutes, and still more preferably, about 15 minutes.

If desired, alternatively, the first and second steps, as outlined above, may be reversed, or only one of the two steps can be used.

Where sterilization occurs by a process other than heat sterilization at a temperature which would cause rupture of the gas filled microspheres, sterilization may occur subsequent to the formation of the gas filled microspheres, and is preferred. For example, gamma radiation may be used before and/or after gas filled microspheres are formed.

Methods of Preparation Using a Gaseous Precursor

In addition to the aforementioned embodiments, gaseous precursors contained in microspheres can be formulated which, upon activation, for example, by exposure to elevated temperature, varying pH, or light, undergo a phase transition from, for example, a liquid, including a liquid entrapped in a microsphere, to a gaseous state, expanding to create the stabilized, homogenous suspensions of the present invention. In preferred embodiments, activation of the gaseous precursor converts gaseous precursor filled microspheres to gas-filled microspheres. This technique is described in detail in copending patent applications Ser. Nos. 08/160,232, filed Nov. 30, 1993 and 08/159,687, filed Nov. 30, 1993, the disclosures of each of which are incorporated herein by reference in their entirety.

The preferred method of activating the gaseous precursor is by exposure to elevated temperature. Activation or transition temperature, and like terms, refer to the boiling point of the gaseous precursor which is the temperature at which the liquid to gaseous phase transition of the gaseous precursor takes place. Useful gaseous precursors are those materials which have boiling points in the range of about −100° C. to 70° C. The activation temperature is particular to each gaseous precursor. An activation temperature of about 37° C., or about human body temperature, is preferred for gaseous precursors of the present invention. Thus, in preferred form, a liquid gaseous precursor is activated to become a gas at 37° C. However, the gaseous precursor may be in liquid or gaseous phase for use in the methods of the present invention.

The methods of preparing the CT imaging contrast agents of the present invention may be carried out below the boiling point of the gaseous precursor such that a liquid is incorporated, for example, into a microsphere. In addition, the methods may be performed at the boiling point of the gaseous precursor such that a gas is incorporated, for example, into a microsphere. For gaseous precursors having low temperature boiling points, liquid precursors may be emulsified using a microfluidizer device chilled to a low temperature. The boiling points may also be depressed using solvents in liquid media to utilize a precursor in liquid form. Further, the methods may be performed where the temperature is increased throughout the process, whereby the process starts with a gaseous precursor as a liquid and ends with a gas.

The gaseous precursor may be selected so as to form the gas in situ in the targeted tissue or fluid, in vivo upon entering the patient or animal, prior to use, during storage, or during manufacture. The methods of producing the temperature-activated gaseous precursor-filled microspheres may be carried out at a temperature below the boiling point of the gaseous precursor. In this embodiment, the gaseous precursor is entrapped within a microsphere such that the phase transition does not occur during manufacture. Instead, the gaseous precursor-filled microspheres are manufactured in the liquid phase of the gaseous precursor. Activation of the phase transition may take place at any time as the temperature is allowed to exceed the boiling point of the precursor. Also, knowing the amount of liquid in a droplet of liquid gaseous precursor, the size of the microspheres upon attaining the gaseous state may be determined.

Alternatively, the gaseous precursors may be utilized to create stable gas-filled microspheres which are pre-formed prior to use. In this embodiment, the gaseous precursor is added to a container housing a suspending and/or stabilizing medium at a temperature below the liquid-gaseous phase transition temperature of the respective gaseous precursor. As the temperature is then increased, and an emulsion is formed between the gaseous precursor and liquid solution, the gaseous precursor undergoes transition from the liquid to the gaseous state. As a result of this heating and gas formation, the gas displaces the air in the head space above the liquid suspension so as to form gas-filled spheres which entrap the gas of the gaseous precursor, ambient gas (e.g. air), or coentrap gas state gaseous precursor and ambient air. This phase transition can be used for optimal mixing and stabilizing of the CT imaging contrast medium. For example, the gaseous precursor, perfluorobutane, can be entrapped in the biocompatible stabilizing compound, and as the temperature is raised, beyond 4° C., which is the boiling point of perfluorobutane, perfluorobutane gas is entrapped in microspheres. As an additional example, the gaseous precursor fluorobutane can be suspended in an aqueous suspension containing, for example, emulsifying and/or thickening agents, such as glycerol or propylene glycol, and vortexed on a commercial vortexer. Vortexing is commenced at a temperature low enough that the gaseous precursor is liquid and is continued as the temperature of the sample is raised past the phase transition temperature from the liquid to gaseous state. In so doing, the precursor converts to the gaseous state during the microemulsification process. In the presence of the appropriate materials, including, for example, stabilizing materials, thickening agents and/or dispersing agents, stable gas-filled microspheres are provided.

Accordingly, the gaseous precursors may be selected to form a gas-filled microsphere in vivo or may be designed to produce the gas-filled microsphere in situ, during the manufacturing process, on storage, or at some time prior to use.

As a further embodiment of this invention, by pre-forming the gaseous precursor in the liquid state into an aqueous emulsion, the maximum size of the microsphere may be estimated by using the ideal gas law, once the transition to the gaseous state is effectuated. For the purpose of making gas-filled microspheres from gaseous precursors, the gas phase is assumed to form instantaneously and substantially no gas in the newly formed microsphere has been depleted due to diffusion into the liquid, which is generally aqueous in nature. Hence, from a known liquid volume in the emulsion, one would be able to predict an upper limit to the size of the gas-filled microsphere.

Pursuant to the present invention, a mixture of a stabilizing material and a gaseous precursor, containing liquid droplets of defined size, may be formulated such that upon reaching a specific temperature, the boiling point of the gaseous precursor, the droplets will expand into gas-filled microspheres of defined size. The defined size represents an upper limit to the actual size because factors such as gas diffusion into solution, loss of gas to the atmosphere, and the effects of increased pressure are factors for which the ideal gas law cannot account.

The ideal gas law and the equation for calculating the increase in volume of the gas bubbles on transition from the liquid to gaseous states is as follows:

$$PV = nRT$$

where

P is pressure in atmospheres (atm);

V is volume in liters (L);

n is moles of gas;

T is temperature in degrees Kelvin (K); and

R is the ideal gas constant (22.4 L-atm/K-mole).

With knowledge of volume, density, and temperature of the liquid in the mixture of liquids, the amount (e.g. number of moles) of liquid precursor as well as the volume of liquid precursor may be calculated which, when converted to a gas, will expand into a microsphere of known volume. The calculated volume will reflect an upper limit to the size of the gas-filled microsphere, assuming instantaneous expansion into a gas-filled microsphere and negligible diffusion of the gas over the time of the expansion.

Thus, for stabilization of the precursor in the liquid state in a mixture wherein the precursor droplet is spherical, the volume of the precursor droplet may be determined by the equation:

$$\text{Volume (sphere)} = 4/3 \, \pi r^3$$

where r is the radius of the sphere.

Thus, once the volume is predicted, and knowing the density of the liquid at the desired temperature, the amount of liquid (gaseous precursor) in the droplet may be determined. In more descriptive terms, the following can be applied:

$$V_{gas} = 4/3 \, \pi (r_{gas})^3$$

by the ideal gas law, $$PV = nRT$$

substituting reveals, $$V_{gas} = nRT/P_{gas}$$

or, $$(A)\ n = 4/3[\pi r_{gas}^3]P/RT$$

amount $n = 4/3\ [\pi r_{gas}^3 P/RT] \cdot MW_n$

Converting back to a liquid volume $$(B)\ V_{liq} = [4/3[\pi r_{gas}^3]P/RT] \cdot MW_n/D]$$

where D is the density of the precursor.

Solving for the diameter of the liquid droplet, $$(C)\ \text{diameter}/2 = [3/4\pi[4/3 \cdot [\pi r_{gas}^3]P/RT]MW_n/D]^{1/3}$$

which reduces to $$\text{Diameter} = 2[[r_{gas}^3]P/RT\ [MW_n/D]]^{1/3}$$

As a further means of preparing microspheres of the desired size for use as CT imaging contrast agents in accordance with the present invention, and with a knowledge of the volume and especially the radius of the stabilizing compound/precursor liquid droplets, one can use appropriately sized filters in order to size the gaseous precursor droplets to the appropriate diameter sphere.

A representative gaseous precursor may be used to form a microsphere of defined size, for example, 10 µm diameter. In this example, the microsphere is formed in the bloodstream of a human being, thus the typical temperature would be 37° C. or 310 K. At a pressure of 1 atmosphere and using the equation in (A), $7.54\times10^{-17}$ moles of gaseous precursor would be required to fill the volume of a 10 μm diameter microsphere.

Using the above calculated amount of gaseous precursor, and 1-fluorobutane, which possesses a molecular weight of 76.11, a boiling point of 32.5° C. and a density of 0.7789 g/mL at 20° C., further calculations predict that $5.74\times10^{-15}$ grams of this precursor would be required for a 10 μm microsphere. Extrapolating further, and with the knowledge of the density, equation (B) further predicts that $8.47\times10^{-16}$ mL of liquid precursor is necessary to form a microsphere with an upper limit of 10 μm.

Finally, using equation (C), a mixture, for example, an emulsion containing droplets with a radius of 0.0272 μm or a corresponding diameter of 0.0544 μm, is formed to make a gaseous precursor filled microsphere with an upper limit of a 10 μm microsphere.

An emulsion of this particular size could be easily achieved by the use of an appropriately sized filter. In addition, as seen by the size of the filter necessary to form gaseous precursor droplets of defined size, the size of the filter would also suffice to remove any possible bacterial contaminants and, hence, can be used as a sterile filtration as well.

This embodiment for preparing gas-filled microspheres used as CT imaging contrast agents in the methods of the present invention may be applied to all gaseous precursors activated by temperature. In fact, depression of the freezing point of the solvent system allows the use of gaseous precursors which would undergo liquid-to-gas phase transitions at temperatures below 0° C. The solvent system can be selected to provide a medium for suspension of the gaseous precursor. For example, 20% propylene glycol miscible in buffered saline exhibits a freezing point depression well below the freezing point of water alone. By increasing the amount of propylene glycol or adding materials such as sodium chloride, the freezing point can be depressed even further.

The selection of appropriate solvent systems may be determined by physical methods as well. When substances, solid or liquid, herein referred to as solutes, are dissolved in a solvent, such as water based buffers, the freezing point is lowered by an amount that is dependent upon the composition of the solution. Thus, as defined by Wall, one can express the freezing point depression of the solvent by the following equation:

$$\ln x_a=\ln\ (1-x_b)=\Delta H_{fus}/R(1/T_o-1/T)$$

where $x_a$ is the mole fraction of the solvent;

$x_b$ is the mole fraction of the solute;

$\Delta H_{fus}$ is the heat of fusion of the solvent; and $T_o$ is the normal freezing point of the solvent.

The normal freezing point of the solvent can be obtained by solving the equation. If $x_b$ is small relative to $x_a$, then the above equation may be rewritten as follows.

$$x^b=\Delta H_{fus}/R[T-T_o/T_oT]\approx\Delta H_{fus}\Delta T/RT_o^2$$

The above equation assumes the change in temperature ΔT is small compared to $T_2$. This equation can be simplified further by expressing the concentration of the solute in terms of molarity, m (moles of solute per thousand grams of solvent). Thus, the equation can be rewritten as follows.

$$X_b=m/[m+1000/m_a]\approx mMa/1000$$

where Ma is the molecular weight of the solvent.

Thus, substituting for the fraction $x_b$:

$$\Delta T=[M_aRT_o^2/1000\Delta H_{fus}]m$$

$$\text{or } \Delta T=K_fm,\ \text{where}$$

$$K_f=M_aRT_o^2/1000\Delta H_{fus}$$

$K_f$ is referred to as the molal freezing point and is equal to 1.86 degrees per unit of molal concentration for water at one atmosphere pressure. The above equation may be used to accurately determine the molal freezing point of gaseous-precursor filled microsphere solutions used in the present invention.

Hence, the above equation can be applied to estimate freezing point depressions and to determine the appropriate concentrations of liquid or solid solute necessary to depress the solvent freezing temperature to an appropriate value.

Methods of preparing the temperature activated gaseous precursor-filled microspheres include:

(a) vortexing and/or shaking an aqueous mixture of gaseous precursor and additional materials as desired, including, for example, stabilizing materials, thickening agents and/or dispersing agents. Optional variations of this method include autoclaving before vortexing or shaking; heating an aqueous mixture of gaseous precursor; venting the vessel containing the mixture/suspension; shaking or permitting the gaseous precursor microspheres to form spontaneously and cooling down the suspension of gaseous precursor filled microspheres; and extruding an aqueous suspension of gaseous precursor through a filter of about 0.22 μm. Alternatively, filtering may be performed during in vivo administration of the microspheres such that a filter of about 0.22 μm is employed;

(b) a microemulsification method whereby an aqueous mixture of gaseous precursor is emulsified by agitation and heated to form, for example, microspheres prior to administration to a patient;

(c) heating a gaseous precursor in a mixture, with or without agitation, whereby the less dense gaseous precursor-filled microspheres float to the top of the solution by expanding and displacing other microspheres in the vessel and venting the vessel to release air; and (d) utilizing in any of the above methods a sealed vessel to hold the aqueous suspension of gaseous precursor and maintaining the suspension at a temperature below the phase transition temperature of the gaseous precursor, followed by autoclaving to raise the temperature above the phase transition temperature, optionally with shaking, or permitting the gaseous precursor microspheres to form spontaneously, whereby the expanded gaseous precursor in the sealed vessel increases the pressure in the vessel, and cooling down the gas-filled microsphere suspension, after which shaking may also take place.

Freeze drying is useful to remove water and organic materials from the stabilizing materials prior to the shaking installation method. Drying installation methods may be used to remove water from microspheres. By pre-entrapping the gaseous precursor in the dried microspheres (i.e. prior to drying) after warming, the gaseous precursor may expand to fill the microsphere. Gaseous precursors can also be used to fill dried microspheres after they have been subjected to vacuum. As the dried microspheres are kept at a temperature below their gel state to liquid crystalline temperature, the drying chamber can be slowly filled with the gaseous precursor in its gaseous state, e.g. perfluorobutane can be used to fill dried microspheres at temperatures above 4° C. (the boiling point of perfluorobutane).

Preferred methods for preparing the temperature activated gaseous precursor-filled microspheres comprise shaking an aqueous solution having a stabilizing material in the presence of a gaseous precursor at a temperature below the liquid state to gas state phase transition temperature of the gaseous precursor. In the case of aqueous solutions which also contain lipid, this is preferably conducted at a temperature below the gel state to liquid crystalline state phase transition temperature of the lipid. The mixture is then heated to a temperature above the liquid state to gas state phase transition temperature of the gaseous precursor which causes the precursor to volatilize and expand. Heating is then discontinued, and the temperature of the mixture is then allowed to drop below the liquid state to gas state phase transition temperature of the gaseous precursor. Shaking of the mixture may take place during the heating step, or subsequently after the mixture is allowed to cool.

Other methods for preparing gaseous precursor-filled microspheres involve shaking an aqueous solution of, for example, a stabilizing material and a gaseous precursor, and separating the resulting gaseous precursor-filled microspheres for use in computed tomography imaging.

Conventional, aqueous-filled liposomes of the prior art are routinely formed at a temperature above the phase transition temperature of the lipids used to make them, since they are more flexible and thus useful in biological systems in the liquid crystalline state. See, for example, Szoka and Papahadjopoulos, *Proc. Natl. Acad. Sci.* 1978, 75, 4194–4198. In contrast, the microspheres made according to preferred embodiments described herein are gaseous precursor filled, which imparts greater flexibility, since gaseous precursors after gas formation are more compressible and compliant than an aqueous solution.

The methods contemplated by the present invention provide for shaking an aqueous solution comprising a stabilizing material, in the presence of a temperature activatable gaseous precursor. Shaking, as used herein, is defined as a motion that agitates an aqueous solution such that gaseous precursor is introduced from the local ambient environment into the aqueous solution. Any type of motion that agitates the aqueous solution and results in the introduction of gaseous precursor may be used for the shaking. Preferably, the shaking is of sufficient force such that a foam is formed within a short period of time, such as 30 minutes, and preferably within 20 minutes, and more preferably, within 10 minutes. The shaking may involve microemulsifying, microfluidizing, swirling (such as by vortexing), side-to-side, or up and down motion. In the case of the addition of gaseous precursor in the liquid state, sonication may be used in addition to the shaking methods set forth above. Further, different types of motion may be combined. Also, the shaking may occur by shaking the container holding the aqueous lipid solution, or by shaking the aqueous solution within the container without shaking the container itself. Further, the shaking may occur manually or by machine. Mechanical shakers that may be used include, for example, a shaker table, such as a VWR Scientific (Cerritos, Calif.) shaker table, a microfluidizer, Wig-L-Bug® (Crescent Dental Manufacturing, Inc., Lyons, Ill.), which has been found to give particularly good results, and a mechanical paint mixer, as well as other known and available equipment. Another means for producigaseous preincludes the action of gaseous precursor emitted under high velocity or pressure. It will also be understood that preferably, with a larger volume of aqueous solution, the total amount of force will be correspondingly increased. Vigorous shaking is defined as at least about 60 shaking motions per minute, and is preferred. Vortexing at about 1000 revolutions per minute is more preferred. Vortexing at 1800 revolutions per minute is even more preferred.

The formation of gaseous precursor filled microspheres upon shaking can be detected by the presence of a foam on the top of the aqueous solution. This is coupled with a decrease in the volume of the aqueous solution upon the formation of foam. Preferably, the final volume of the foam is at least about two times the initial volume of the aqueous solution. More preferably, the final volume of the foam is at least about three times the initial volume of the aqueous solution, with a final volume of the foam of at least about four times the initial volume of the aqueous solution being even more preferred. Still more preferred, all of the aqueous solution is converted to foam.

The required duration of shaking time may be determined by detection of the formation of foam. For example, 10 mL of solution in a 50 mL centrifuge tube may be vortexed for approximately 15 to 20 minutes or until the viscosity of the gaseous precursor-filled microspheres becomes sufficiently thick so that it no longer clings to the side walls as it is swirled. At this time, the foam may cause the solution containing the gaseous precursor-filled microspheres to raise to a level of 30 to 35 mL.

According to the methods contemplated by the present invention, the presence of gas, such as air, may also be provided by the local ambient atmosphere. The local ambient atmosphere can include the atmosphere within a sealed container, or in an unsealed container, the external environment. Alternatively, for example, a gas may be injected into or otherwise added to the container having the aqueous lipid solution or into the aqueous lipid solution itself in order to provide a gas other than air. Gases that are lighter than air are generally added to a sealed container while gases heavier than air can be added to a sealed or an unsealed container. Accordingly, the present invention includes co-entrapment of air and/or other gases along with gaseous precursors.

Hence, the stabilized microsphere precursors described above, can be used in the same manner as the other stabilized microspheres used in the present invention, once activated by application to the tissues of a host, where such factors as temperature or pH may be used to cause generation of the gas. It is preferred that the gaseous precursors undergo phase transitions from liquid to gaseous states at near the normal body temperature of said host, and are thereby activated, for example, by the in vivo temperature of the host so as to undergo transition to the gaseous phase therein. This can occur where, for example, the host tissue is human tissue having a normal temperature of about 37° C. and the gaseous precursors undergo phase transitions from liquid to gaseous states near 37° C.

All of the above embodiments involving preparations of the stabilized suspensions, including suspensions of gas and/or gaseous precursor filled microspheres, may be sterilized by autoclave or sterile filtration if these processes are performed before the installation step or prior to temperature mediated conversion of the temperature sensitive gaseous precursors within the suspension. Alternatively, one or more anti-bactericidal agents and/or preservatives may be included in the formulation of the contrast medium, such as sodium benzoate, quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, monothioglycerol, potassium benzoate, potassium metabisulfite, potassium sorbate, sodium bisulfite, sulfur dioxide, and organic mercurial salts. Such sterilization, which may also be achieved by other conventional means, such as by irradiation, will be necessary where the stabilized microspheres are used for imaging under invasive circumstances, e.g., intravascularly or intraperitoneally. The appropriate means of sterilization will be apparent to the artisan based on the present disclosure.

The contrast medium of the present invention is generally stored as an aqueous suspension, but the contrast medium can be stored as a dried powder ready to be reconstituted prior to use in the case of dried microspheres.

Methods of Use

As discussed above, the stabilized suspensions of the present invention, including suspensions of gas and/or gaseous precursor filled microspheres, are useful as contrast agents for computed tomography (CT) imaging, including CT angiography (CTA) imaging. It is contemplated that the present stabilized suspensions are useful as contrast agents in connection with other diagnostic methodologies, including, for example, magnetic resonance (MR) imaging and magnetic resonance angiography (MRA).

In accordance with the present invention, there is provided a method of imaging one or more regions of a patient. The present invention provide also imaging methods which involve diagnosing the presence or absence of diseased tissue in a patient. The imaging methods of the present invention can be carried out by administering a contrast medium, in the form of a stabilized suspension, to a patient. The patient is scanned using computed tomography imaging, or other imaging methodologies, to obtain visible images of an internal region of a patient and/or of any diseased tissue in that region. By region of a patient, it is meant the whole patient or a particular area or portion of the patient. The contrast medium is particularly useful in providing images of the gastrointestinal region, but can also be employed more broadly such as in imaging the vasculature or in other ways as will be readily apparent to those skilled in the art. The phrase gastrointestinal region or gastrointestinal tract, as used herein, includes the region of a patient defined by the esophagus, stomach, small and large intestines and rectum. The phrase vasculature, as used herein, denotes the blood vessels in the body or in an organ or part of the body. The patient can be any type of mammal, but most preferably is a human.

As one skilled in the art would recognize, administration of the stabilized suspensions of the present invention can be carried out in various fashions, such as intravascularly, orally, intrarectally, intravaginally, intravesicularly, intraperitonealy, intracochlearly, intragenitouterally, and the like, using a variety of dosage forms. When the region to be scanned is the gastrointestinal region, administration of the suspensions of the present invention is preferably carried out orally or rectally. The useful dosage to be administered and the particular mode of administration will vary depending upon the age, weight and the particular mammal and region thereof to be scanned, and the particular contrast medium of the invention to be employed. Typically, dosage is initiated at lower levels and increased until the desired contrast enhancement is achieved. Various combinations of the stabilized suspensions may be used to alter properties as desired, including viscosity, osmolarity or palatability. In carrying out the imaging methods of the present invention, the contrast medium can be used alone, or in combination with diagnostic, therapeutic or other agents. Such other agents include excipients such as flavoring or coloring materials. CT imaging techniques which are employed are conventional and are described, for example, in *Computed Body Tomography*, Lee, J. K. T., Sagel, S. S., and Stanley, R. J., eds., 1983, Ravens Press, New York, N.Y., especially the first two chapters thereof entitled "*Physical Principles and Instrumentation*", Ter-Pogossian, M. M., and "*Techniques*", Aronberg, D. J., the disclosures of which are incorporated by reference herein in their entirety.

The routes of administration and areas of usefulness of the present suspensions are not limited merely to the blood volume space, including the vasculature. CT imaging can be achieved with the suspensions of the present invention if ingested orally to image the gastrointestinal (GI) tract. Alternatively, rectal administration of these stabilized suspensions can result in excellent imaging of the lower GI tract, including the rectum, descending colon, transverse colon, and ascending colon, as well as the appendix. The suspensions of the present invention, and especially gas filled and gaseous precursor filled microspheres, are particularly well suited for imaging the GI tract. For example, suspensions comprising gas filled or gaseous precursor filled microspheres can be administered to the patient orally or rectally. It has been found that suspensions of gaseous precursor filled microspheres are generally more palatable than suspensions of gas filled microspheres. Accordingly, in the case of oral administration, suspensions of gaseous precursor filled microspheres are preferred. In the case of suspensions of microspheres filled with a gaseous precursor having a transition temperature at near body temperature, the gaseous precursor filled microspheres are desirably and conveniently converted to gas filled microspheres within the GI tract of the patient.

In addition to the areas of the GI tract which can be imaged with the suspensions of the present invention, including the rectum, descending colon, transverse colon, ascending colon, and appendix, it is contemplated that the ileum, and conceivably the jejunum, can be imaged by the methods described herein by way of rectal administration. In addition, direct intraperitoneal administration may be achieved to visualize the peritoneum. It is also contemplated that the stabilized suspensions may be administered directly into the ear canals such that one can visualize the canals as well as the Eustachian tubes and, if a perforation exists, the inner ear. It is also contemplated that the stabilized suspensions may be administered intranasally to aid in the visualization of the nasal septum as well as the nasal sinuses by CT.

Other routes of administration of the suspensions of the present invention, and tissue areas whose imaging is enhanced thereby include, for example, (i) intranasally for imaging the nasal passages and sinuses, including the nasal region and sinuses and sinusoids; (ii) intranasally and orally for imaging the remainder of the respiratory tract, including the trachea, bronchus, bronchioles, and lungs; (iii) intracochlearly for imaging the hearing passages and Eustachian tubes, tympanic membranes and outer and inner ear and ear canals; (iv) intraocularly for imaging the regions associated with vision; (v) intraperitoneally to visualize the peritoneum; and (vi) intravesicularly, i.e., through the bladder, to image all regions of the genitourinary tract including, for example, the urethra, bladder, ureters, kidneys and renal vasculature and beyond, for example, to perform cystography or to confirm the presence of ureteral reflux.

The invention is further described in the following examples. Examples 1 to 168 are actual examples. Examples 169 to 170 are prophetic examples. These examples are for illustrative purposes only, and are not to be construed as limiting the appended claims.

The following examples (Examples 1 to 10) describe the preparation of various stabilized suspensions within the scope of the present invention. Various of these examples (Examples 1 to 6) also describe methods which are within the scope of the present invention and which involve imaging internal regions of mammals using CT. Example 7 describes methods which are within the scope of the present invention and which involve imaging internal regions of mammals using MR.

EXAMPLE 1

To purified water (730 mL) were added 0.5 wt % methylcellulose (Spectrum, Houston Tex.), Poloxamer F68 (500 ppm) (Spectrum, Houston Tex.), Polysorbate 40 (200 ppm) (Spectrum, Houston, Tex.), simethicone (500 ppm) (Dow Corning, Midland, Mich.) and 0.1% potassium sorbate (Spectrum, Houston Tex.). The mixture was mixed for 5 minutes with a Silverson L4RT mixer (Silverson Machine LTD, Waterside, England) with the general assembly and the square hole high shear screen set at 5000 rpm. The resulting mixture was cooled to 7° C. in an ice bath. Perfluoropentane (5 mL) (PCR Chemicals Inc., Gainsville, Fla.) was added to the cooled mixture. The mixture was then agitated for 1 minute with the same mixer and screen as before except the speed was adjusted to a higher setting (10,300 rpm). The resulting stabilized suspension of perfluoropentane had a viscosity of 30.8 cps as measured by a Gilmont Instruments size No. 2 falling ball viscosimeter, model GV-2200 (Gilmont Instr., Barrington, Ill.). The number weighted mean particle size was 4.58 µm as measured using an AccuSizer 770 optical particle sizer (Particle Sizing Systems Inc., Santa Barbara, Calif.).

Approximately 500 mL of the stabilized suspension was administered to a dog (17.25 kg) which had been kept NPO (none per oral) for 24 hours. This corresponds to a dosage of 30 mL/kg. The suspension was dispensed to the dog in a dish over a two hour period. Prior to CT imaging, the dog was anesthetized with a dose of 0.25 cc/kg sodium pentothal and kept under anesthesia with isoflurane. CT imaging was performed with a Toshiba 900S CT scanner (Toshiba Medical Systems, Nasu, Japan) and the images were recorded on X-ray film. Superior images of the bowel were obtained. The entire bowel was visualized as lumena filled with homogeneous black contrast. The mucosal surfaces were readily discerned throughout the entire bowel.

CT Angiography (CTA) was performed on a Picker 2000 CT scanner (Picker Medical Systems, Cleveland, Ohio) with a dose of 0.5 mL/kg iohexol (Sanofi Winthrop, New York, N.Y.) to create positive contrast in the abdominal vasculature. CTA was acquired with a slice thickness of 5 mm with a pitch of 1.25 and power settings of 130 kV and 100 ma on a modified spiral pancreas setting. Superior images of the abdominal vasculature were obtained. No interference with visualization of the blood vessels was caused by the black bowel. By comparison, CTA performed after iohexol (I.V.) in subjects administered oral barium sulfate was markedly degraded by density in the bowel overlapping and obscuring the abdominal vasculature.

EXAMPLE 2

Poloxamer F68 (0.25 g), simethicone (0.25 g), polysorbate 40 (0.1 g), sodium benzoate (0.5 g), fructose (10 g), methylcellulose (5 g) and purified water (484 g) were combined and the resulting mixture was mixed until homogeneous using a Silverson L4RT mixer equipped with the 1" tubular assembly and the square hole high-shear screen set at 8000 rpm. The homogenous mixture was cooled to 4° C. in an ice bath and perfluoropentane (3 mL) was added. The mixture was then mixed for 1 minute with high shearing using the same mixer as above and with the assembly set at a higher speed (12,000 rpm). The resulting stabilized suspension had a viscosity of 103 cps as measured by a Gilmont Instruments size No. 2 falling ball viscosimeter model GV-2200 (Gilmont Instr., Barrington, Ill.). The number weighted mean particle size was 4.07 µm as measured using an AccuSizer 770 optical particle sizer (Particle Sizing Systems Inc., Santa Barbara, Calif.).

A Sprague-Dawley rat (250 g) that had been NPO for 24 hr was gavaged with the mixture (4 mL) and imaged at 1 and 1.5 hours with a Toshiba 900S CT machine which was set at 100 milliamps, 140 kilovolts and 4 mm slice thickness. Homogeneous negative contrast of the GI tract was observed.

EXAMPLE 3

Poloxamer F68 (0.125 g), simethicone (0.125 g), polysorbate 40 (0.05 g), sodium benzoate (0.25 g), fructose (5 g), Veegum™ (5 g) (Spectrum, Houston, Tex.) and purified water (239 g) were combined and the resulting mixture was mixed until homogeneous using a Silverson L4RT mixer equipped with the 1" tubular assembly and the square hole high-shear screen set at 8000 rpm. The homogenous mixture was cooled to 4° C. in an ice bath and perfluoropentane (1.6 mL) was added. The mixture was then mixed for 1 minute with high shearing using the same mixer as above and with the assembly set at a higher speed (12,000 rpm). The resulting stabilized suspension had a viscosity of 5.6 cps as measured by a Gilmont Instruments size No. 2 falling ball viscosimeter model GV-2200 (Gilmont Instr., Barrington, Ill.). The number weighted mean particle size was 2.67 µm as measured using an AccuSizer 770 optical particle sizer (Particle Sizing Systems Inc., Santa Barbara, Calif.).

A Sprague-Dawley rat (250 g) that had been NPO for 24 hrs was gavaged with the suspension (4 mL) and imaged at 1 and 1.5 hours with a Toshiba 900S CT machine (Toshiba Medical Systems, Nasu, Japan) set at 100 milliamps, 140 kilovolts and 4 mm slice thickness. Homogeneous negative contrast of the GI tract was observed.

EXAMPLE 4

Poloxamer F68 (0.125 g), simethicone (0.125 g), polysorbate 40 (0.05 g), sodium benzoate (0.25 g), fructose (5 g), xanthan gum (2.5 g) (Kelco, San Diego, Calif.) and purified water (242 g) were combined until homogeneous using a Silverson L4RT mixer equipped with the 1" tubular assembly and the square hole high-shear screen set at 8000 rpm. The homogenous mixture was cooled to 4° C. in an ice bath and perfluoropentane (1.6 mL) was added. The mixture was then mixed for 1 minute with high shearing using the same mixer as above with the assembly set at a higher speed (12,000 rpm). The viscosity of the resulting stabilized suspension was too thick to measure with a Gilmont Instruments size No. 2 falling ball viscosimeter model GV-2200 (Gilmont Instr., Barrington, Ill.). The number weighted mean particle size was 4.06 µm as measured using an AccuSizer 770 optical particle sizer (Particle Sizing Systems Inc., Santa Barbara, Calif.).

A Sprague-Dawley rat (250 g) that had been NPO for 24 hr was gavaged with the suspension (4 mL) and imaged at 1 and 1.5 hours with a Toshiba 900S CT machine (Toshiba Medical Systems, Nasu, Japan) which was set at 100 milliamps, 140 kilovolts and 4 mm slice thickness. Extremely homogeneous negative contrast, at a density approaching that of air, was observed in the GI tract.

EXAMPLE 5

Poloxamer F68 (0.3125 g), simethicone (0.3125 g), polysorbate 40 (0.125 g), sodium benzoate (0.625 g), fructose (18 g) and purified water (500 g) were combined and the resulting mixture was mixed until homogeneous using a Silverson L4RT mixer equipped with the 1" tubular assembly and the square hole high-shear screen set at 8000 rpm. The pH of the homogenous mixture was adjusted to pH 4 with 1N HCl (Fisher Chemical Supply, Fair Lawn, N.J.) and the mixture was cooled to 4° C. in an ice bath. The cooled mixture was placed in a M-110T Microfluidizer (Mircofluidics Corp., Newton, Mass.) equipped with a cooling chamber through which a water/methyl alcohol solution was cycled to cool the fluidized mixture to 10° C. while operating at 15,000 psi. The cooled mixture was cycled approximately 2 passes and then perfluoropentane (3.9 mL) was added to the cycling mixture. The M-110T Microfluidizer was then allowed to cycle 500 times. A 2.5% solution of methylcellulose was prepared by the addition of methylcellulose (12.5 g) to purified water (487 g) which was mixed using a Silverson L4RT mixer (Silverson Machine LTD, Waterside, England) with the general assembly and the square hole high shear screen set at 5000 rpm. The cooled mixture prepared above (200 mL) was added to the 2.5% methylcellulose solution (50 mL) and blended by stirring. The resulting stabilized suspension had a viscosity of 15.5 cps as measured by a Gilmont Instruments size No. 2 falling ball viscosimeter model GV-2200 (Gilmont Instr., Barrington, Ill.). The number weighted mean particle size was 1.76 µm as measured using an AccuSizer 770 optical particle sizer (Particle Sizing Systems Inc., Santa Barbara, Calif.).

Two Sprague-Dawley rats (250 g each) which were NPO for 24 hr were each gavaged with the blended suspension (4 mL) and imaged at 1 and 1.5 hours with a Toshiba 900S CT machine (Toshiba Medical Systems, Nasu, Japan) which was set at 100 milliamps, 140 kilovolts and 4 mm slice thickness. Extremely homogeneous negative contrast, at a density approaching that of air, was observed in the GI tract.

EXAMPLE 6

Poloxamer F68 (0.195 g), simethicone (0.195 g) and potassium sorbate (0.432 g) were combined and brought to 300 g with purified water. The resulting mixture was mixed until homogeneous using a Braun Multipractic Hand Blender (Braun Inc, Lynnfield, Mass.). The pH of the homogenous mixture was adjusted to pH 6 with 1N HCl (Fisher Chemical Supply, Fair Lawn, N.J.) and the mixture was cooled to 4° C. in an ice bath. A portion of the cooled homogenous mixture (250 mL) was placed in a M-110T Microfluidizer (Mircofluidics Corp., Newton, Mass.) equipped with a cooling chamber through which a water/methyl alcohol solution was cycled to cool the fluidized mixture to 10° C. while operating at 15,000 psi. The homogenous mixture was cycled approximately 2 passes and then perfluoropentane (1.9 mL) was added to the cycling mixture. The M-110T Microfluidizer was then allowed to cycle 250 times. A portion of this mixture (187.5 mL) was added to a 1% xanthan gum solution (62.5 mL) and the resulting mixture was blended by stirring to provide a stabilized suspension. The suspension had a viscosity of 16.1 cps as measured by a Gilmont Instruments size No. 2 falling ball viscosimeter model GV-2200 (Gilmont Instr., Barrington, Ill.). The number weighted mean particle size was 6.50 µm as measured using an AccuSizer 770 optical particle sizer (Particle Sizing Systems Inc., Santa Barbara, Calif.).

A Sprague-Dawley rat (250 g) that had been NPO for 24 hr was gavaged with the suspension (4 mL) and the rat was imaged at 1.5 and 2 hours with a Toshiba 900S CT machine (Toshiba Medical Systems, Nasu, Japan) which was set at 100 milliamps, 140 kilovolts and 4 mm slice thickness. Extremely homogeneous negative contrast, at a density approaching that of air, was observed in the GI tract.

EXAMPLE 7

Into a 15 mL polypropylene screw cap tube (VWR, West Chester, Pa.) were introduced water (7.3 mL), a 1% solution of xanthan gum (1 mL), soy oil (1 mL), a 1% aqueous solution of sodium lauryl sulfate (300 µL) (Duponol C, Witco Corp., New York, N.Y.), a 1% aqueous solution of polysorbate 40 (200 µL), a 1% aqueous solution of potassium sorbate (100 µL), simethicone (5 µL), and perfluoropentane (100 µL). The mixture was agitated using a Vortex-Genie 2 (Scientific Industries Inc., Franklin Lakes, N.J.) on full speed for 1 minute, thereby creating a stabilized suspension.

A Sprague-Dawley rat (250 g) that had been NPO for 24 hr was gavaged with the suspension (4 mL). After one hour, the rat was anesthetized with 1.3 cc/kg of a 10:1 mixture of ketamine HCl (Ketaset, Aveco Co. Inc., Fort Dodge, Iowa) and acepromazine maleate (PromAce, Aveco Co. Inc., Fort Dodge, Iowa). The rat was imaged using multiple protocols in a GE Signa 1.5 Tesla MR scanner (GE Signa, Milwaukee, Wis.) using the extremity coil. Four protocols were used: MEMP, VEMP, GRASS and Fast GRASS. Settings for MEMP imaging were as follows: 250 TR, 14 ms TE (Auto), 11 cm FOV, 4 mm slice thickness, 1 mm gap, 4 NEX and a 256×192 matrix. Settings for VEMP imaging were as follows: 2500 ms TR, 19/80 ms TE, 11 cm FOV, 4 mm slice thickness, 1 mm gap, 1 NEX and a 256×192 matrix. Settings for GRASS imaging were as follows: 13.1 ms TR, 4.2 ms TE, 20 degree flip angle, 15 cm FOV, 4 mm slice thickness, 1 mm gap, 2 NEX and a 256×192 matrix. Settings for Fast GRASS imaging were as follows: 100 ms TR, 6 ms TE, 30 degree flip angle, 11 cm FOV, 4 mm slice thickness, 1 mm gap, 1 NEX and a 256×192 matrix. The MR images showed homogeneous low signal intensity (signal voids) within the entire GI tract. The mucosal detail was excellent in the MEMP and VEMP images and all of the images were free of susceptibility artifacts. The experiments with MR imaging verify that the compositions of the present invention function as an effective negative (black) contrast agent for MR.

EXAMPLE 8

Poloxamer F68 (0.25 g), simethicone (0.25 g), polysorbate 40 (0.05 g), sodium benzoate (0.5 g), fructose (10 g), methyl cellulose (2.5 g) and purified water (486 g) were combined and the resulting mixture was mixed until homogeneous (10 minutes) using a Silverson L4RT mixer equipped with a 1 inch tubular assembly and a square hole high-shear screen set at 5000 rpm. A portion of this homogenous mixture (250 mL) was cooled to 4° C. in an ice bath to which perfluoropentane (0.16 mL) was added. The resulting mixture was mixed for 1 minute with high shearing using the same mixer and assembly as above at a higher speed setting (12,900 rpm). A first portion of this sheared suspension was sized for particles using an AccuSizer 770 optical particle sizer (Particle Sizing Systems Inc., Santa Barbara, Calif.). A second portion of the sheared suspension was also similarly sized. After 30 days, the sheared suspension, which had become non-homogenous, was resuspended by agitation and sized again. Comparison of the various sizings showed little change in the particle distributions.

EXAMPLE 9

Poloxamer F68 (0.25 g), simethicone (0.25 g), polysorbate 40 (0.05 g), sodium benzoate (0.5 g), fructose (10 g), Viscarin GP-209 carrageenan (1.25 g) (FMC Corp., Philadelphia, Pa.) and purified water (487 g) were combined and the resulting mixture was mixed until homogeneous (10 minutes) using a Silverson L4RT mixer equipped with the 1 inch tubular assembly and the square hole high-shear screen set at 5000 rpm. The pH of the homogenous mixture was adjusted to pH 4 with 1N HCl. A portion of this mixture (250 mL) was cooled to 4° C. in an ice bath and perfluoropentane (0.16 mL) was added. The resulting mixture was then mixed for 1 minute with high shearing using the same mixer and assembly at high speed (12,900 rpm). The resulting stabilized suspension had a viscosity of 15.1 cps as measured by a Gilmont Instruments size No. 2 falling ball viscosimeter model GV-2200 (Gilmont Instr., Barrington, Ill.). The number weighted mean particle size was 4.16 μm as measured using an AccuSizer 770 optical particle sizer (Particle Sizing Systems Inc., Santa Barbara, Calif.).

EXAMPLE 10

Poloxamer F68 (0.25 g), simethicone (0.25 g), polysorbate 40 (0.05 g), sodium benzoate (0.5 g), fructose (10 g), Kelgum (1.25 g) (Kelco, San Diego, Calif.) and purified water (487 g) were combined and the resulting mixture was mixed until homogeneous (10 minutes) using the Silverson L4RT mixer equipped with the 1 inch tubular assembly and the square hole high-shear screen at 5000 rpm. The pH of the homogenous mixture was adjusted to pH 4 with 1N HCl. A portion of this mixture (250 mL) was cooled to 4° C. in an ice bath and perfluoropentane (0.16 mL) was added. The resulting mixture was mixed for 1 minute with high shearing using the same mixer and assembly as above, set at a higher speed (12,900 rpm). The resulting stabilized suspension had a viscosity of 8.6 cps as measured by a Gilmont Instruments size No. 2 falling ball viscosimeter model GV-2200 (Gilmont Instr., Barrington, Ill.). The number weighted mean particle size was 3.62 μm as measured using an AccuSizer 770 optical particle sizer (Particle Sizing Systems Inc., Santa Barbara, Calif.).

Examples 11 to 167 are set forth in the following table.

TABLE 3

| Example No. | Gaseous Precursor (%) | Stabilizing Material Surfactant (A) (ppm) | Stabilizing Material Surfactant (B) (ppm) | Stabilizing Material Surfactant (C) (ppm) | Dispersing Agent (ppm) | Thickening Agent (%) | Auxiliary Materials Oils (%) | Auxiliary Materials Preservative (ppm) | Auxiliary Materials Sweetening Agent | Agitating Method |
|---|---|---|---|---|---|---|---|---|---|---|
| 11 | PFH (1) | CTAB* | — | — | Simeth (500) | — | Soy (10) | — | — | Vortex |
| 12 | PFH (1) | SLS (200) | — | — | Simeth (500) | — | Soy (10) | — | — | Vortex |
| 13 | PFH (1) | L64 (100) | — | — | Simeth (500) | — | Soy (10) | — | — | Vortex |
| 14 | PFH (1) | SLS (500) | — | — | Simeth (500) | — | Soy (5) | — | — | Vortex |
| 15 | PFH (1) | SLS (100) | — | — | Simeth (500) | — | — | — | — | Vortex |
| 16 | PFH (1) | SLS (200) | — | — | Simeth (500) | — | Soy (5) | — | — | Vortex |
| 17 | PFH (1) | SLS (500) | — | — | Simeth (500) | — | Soy (5) | — | — | Vortex |
| 18 | PFH (1) | SLS (1000) | — | — | Simeth (500) | — | Soy (5) | — | — | Vortex |
| 19 | PFH (1) | SLS (100) | — | — | Simeth (500) | — | Soy (10) | — | — | Vortex |
| 20 | PFH (1) | SLS (100) | — | — | Simeth (500) | — | Soy (10) | — | — | Vortex |
| 21 | PFH (1) | SLS (100) | — | — | Simeth (500) | — | Soy (20) | — | — | Vortex |
| 22 | PFH (1) | SLS (200) | — | — | Simeth (500) | — | Soy (10) | — | — | Vortex |
| 23 | PFH (1) | SLS (200) | — | — | Simeth (500) | Corn Syrup (10) | Soy (10) | — | — | Vortex |
| 24 | PFH (1) | SLS (200) | — | — | Simeth (500) | Xanthan Gum (0.2) | Soy (10) | — | — | Vortex |
| 25 | PFH (1) | SLS (200) | — | — | Simeth (500) | Methyl Cellulose (1) | Soy (10) | — | — | Vortex |
| 26 | PFP (1) | SLS (200) | — | — | Simeth (500) | Xanthan Gum (0.2) | Soy (10) | — | — | Vortex |
| 27 | PFP (1) | SLS (300) | — | — | Simeth (500) | Xanthan Gum (0.2) | Soy (10) | — | — | Vortex |
| 28 | PFP (1) | SLS (200) | — | — | Simeth (500) | Xanthan Gum (0.2) | Soy (15) | — | — | Vortex |
| 29 | PFP (1) | SLS (300) | PS 40 (50) | — | Simeth (500) | — | Soy (10) | — | — | Vortex |
| 30 | PFP (1) | SLS (300) | PS 40 (100) | — | Simeth (500) | — | Soy (10) | — | — | Vortex |
| 31 | PFP (1) | SLS (300) | PS 40 (200) | — | Simeth (500) | — | Soy (10) | — | — | Vortex |
| 32 | PFP (1) | SLS (300) | PS 80 (50) | — | Simeth (500) | — | Soy (10) | — | — | Vortex |
| 33 | PFP (1) | SLS (300) | PS 80 (100) | — | Simeth (500) | — | Soy (10) | — | — | Vortex |
| 34 | PFP (1) | SLS (300) | PS 80 (200) | — | Simeth (500) | — | Soy (10) | — | — | Vortex |
| 35 | PFP (1) | SLS (300) | PS 40 (200) | — | Simeth (500) | Xanthan Gum (0.2) | Soy (10) | — | — | Vortex |
| 36 | PFP (1) | SLS (300) | PS 40 (200) | — | Simeth (500) | Methyl Cellulose (1) | Soy (10) | — | — | Vortex |
| 37 | PFP (1) | SLS (300) | PS 40 (200) | — | Simeth (500) | Pectin (1) | Soy (10) | Sorbate (100) | — | Vortex |
| 38 | PFP (1) | SLS (300) | PS 40 (200) | — | Simeth (500) | Xanthan Gum (0.2) | Soy (10) | Sorbate (100) | — | Vortex |
| 39 | — | SLS (300) | PS 40 (200) | — | — | — | Soy (10) | Sorbate (100) | — | Vortex |
| 40 | PFP 2 | SLS (100) | — | — | — | Xanthan Gum (0.2) | Soy (10) | Sorbate (100) | Microfluidize | |
| 41 | PFP 2 | SLS (200) | — | — | — | Xanthan Gum (0.2) | Soy (10) | Sorbate (100) | Microfluidize | |
| 42 | PFP (1) | SLS (100) | — | — | Simeth (500) | — | Soy (10) | Sorbate (100) | — | Handblender |

TABLE 3-continued

Example 12

| Example No. | Gaseous Precursor (%) | Stabilizing Material Surfactant (A) (ppm) | Stabilizing Material Surfactant (B) (ppm) | Stabilizing Material Surfactant (C) (ppm) | Dispersing Agent (ppm) | Thickening Agent (%) | Oils (%) | Auxiliary Materials Preservative (ppm) | Auxiliary Materials Sweetening Agent | Agitating Method |
|---|---|---|---|---|---|---|---|---|---|---|
| 43 | PFP (1) | SLS (100) | — | — | Simeth (500) | Xanthan Gum (0.1) | Soy (10) | Sorbate (100) | — | Handblender |
| 44 | PFP (1) | SLS (200) | — | — | Simeth (500) | — | Soy (10) | Sorbate (100) | — | Handblender |
| 45 | PFP (1) | SLS (200) | — | — | Simeth (500) | — | Soy (5) | Sorbate (100) | — | Handblender |
| 46 | PFP (1) | SLS (100) | — | — | Simeth (500) | — | Soy (5) | Sorbate (100) | — | Handblender |
| 47 | — | SLS (100) | — | — | Simeth (500) | Xanthan Gum (0.05) | Soy (5) | Sorbate (100) | — | Handblender |
| 48 | PFP (1) | SLS (100) | — | — | Simeth (500) | Xanthan Gum (0.05) | Soy (5) | Sorbate (100) | — | Handblender |
| 49 | PFP (1) | — | PS 40 (100) | — | Simeth (500) | — | Soy (5) | Sorbate (100) | — | Handblender |
| 50 | — | SLS (200) | — | — | Simeth (500) | Xanthan Gum (0.1) | Soy (5) | Sorbate (100) | — | Microfluidize |
| 51 | PFP (1) | SLS (200) | — | — | Simeth (500) | Xanthan Gum (0.1) | Soy (5) | Sorbate (100) | — | Microfluidize |
| 52 | — | SLS (200) | — | — | Simeth (500) | Xanthan Gum (0.1) | Soy (5) | Sorbate (100) | — | Microfluidize |
| 53 | PFP (1) | SLS (200) | — | — | Simeth (500) | Xanthan Gum (0.1) | Soy (5) | Sorbate (100) | — | Microfluidize |
| 54 | — | Zonyl™ FSO (500) | — | — | — | — | — | — | — | Microfluidize |
| 55 | PFP (1) | Zonyl™ FSO (500) | — | — | — | — | — | — | — | Microfluidize |
| 56 | — | Zonyl™ FSN (500) | — | — | — | — | — | — | — | Microfluidize |
| 57 | PFP (1) | Zonyl™ FSN (500) | — | — | — | — | — | — | — | Microfluidize |
| 58 | — | Zonyl™ FSO (500) | SLS (200) | — | — | — | — | — | — | Microfluidize |
| 59 | PFP (1) | Zonyl™ FSO (500) | SLS (200) | — | — | — | — | — | — | Microfluidize |
| 60 | — | Zonyl™ FSO (500) | — | — | — | — | Soy (5) | — | — | Microfluidize |
| 61 | PFP (1) | Zonyl™ FSO (500) | — | — | — | — | Soy (5) | — | — | Microfluidize |
| 62 | — | Zonyl™ FSN (100) | SLS (100) | — | — | — | — | Sorbate (100) | — | Microfluidize |
| 63 | PFP (1) | Zonyl™ FSN (100) | SLS (100) | — | — | — | — | Sorbate (100) | — | Microfluidize |
| 64 | — | Zonyl™ FSN (100) | PS 40 (100) | — | — | — | — | Sorbate (100) | — | Microfluidize |
| 65 | PFP (1) | Zonyl™ FSN (100) | PS 40 (100) | — | — | — | — | Sorbate (100) | — | Microfluidize |
| 66 | — | Zonyl™ FSN (100) | PS 40 (100) | — | Simeth (500) | — | — | Sorbate (100) | — | Microfluidize |
| 67 | PFP (1) | Zonyl™ FSN (100) | PS 40 (100) | — | Simeth (500) | — | — | Sorbate (100) | — | Microfluidize |

TABLE 3-continued

Example 12

| Example No. | Gaseous Precusor (%) | Stabilizing Material Surfactant (A) (ppm) | Stabilizing Material Surfactant (B) (ppm) | Stabilizing Material Surfactant (C) (ppm) | Dispersing Agent (ppm) | Thickening Agent (%) | Oils (%) | Auxiliary Materials Preservative (ppm) | Auxiliary Materials Sweetening Agent | Agitating Method |
|---|---|---|---|---|---|---|---|---|---|---|
| 68 | — | Zonyl ™ FSN (100) | Zonyl ™ FSO (100) | — | Simeth (500) | — | — | Sorbate (100) | — | Microfluidize |
| 69 | PFP (1) | Zonyl ™ FSN (100) | Zonyl ™ FSO (100) | — | Simeth (500) | — | — | Sorbate (100) | — | Microfluidize |
| 70 | — | Pol F68 (100) | — | — | Simeth (500) | — | Soy (1) | — | — | Microfluidize |
| 71 | PFP (1) | Pol F68 (100) | — | — | Simeth (500) | — | Soy (1) | — | — | Microfluidize |
| 72 | — | Pol F68 (100) | — | — | Simeth (500) | — | Soy (1) | — | — | Microfluidize |
| 73 | PFP (1) | Pol F68 (100) | Zonyl ™ FSN (100) | — | Simeth (500) | — | — | — | — | Microfluidize |
| 74 | — | Zonyl ™ FSN (100) | Zonyl ™ FSO (100) | SLS (100) | Simeth (500) | Xanthan Gum (0.2) | Soy (1) | Sorbate (100) | — | Microfluidize |
| 75 | PFP (1) | Zonyl ™ FSN (100) | Zonyl ™ FSO (100) | SLS (100) | Simeth (500) | Xanthan Gum (0.2) | Soy (1) | Sorbate (100) | — | Microfluidize |
| 76 | — | Zonyl ™ FSN (100) | Zonyl ™ FSO (100) | SLS (100) | Simeth (500) | Methyl Cellulose (0.1) | Soy (1) | Sorbate (100) | — | Microfluidize |
| 77 | PFP (1) | Zonyl ™ FSN (100) | Zonyl ™ FSO (100) | SLS (100) | Simeth (500) | Methyl Cellulose (0.1) | Soy (1) | Sorbate (100) | — | Microfluidize |
| 78 | PFP (1) | SLS (100) | — | — | — | — | Soy (1) | — | — | Microfluidize |
| 79 | PFP (1) | SLS (100) | — | — | — | — | Soy (1) | — | — | Microfluidize |
| 80 | PFP 2.5 | — | — | — | — | Xanthan Gum (0.2) | — | — | — | syringe |
| 81 | PFP (1) | — | — | — | — | Methyl Cellulose (0.25) | — | — | — | syringe |
| 82 | PFP (1) | — | — | — | — | Gelatin (0.5) | — | — | — | syringe |
| 83 | PFP (1) | — | — | — | — | Methyl Cellulose (0.25) | — | — | — | syringe |
| 84 | PFP (1) | — | — | — | — | Xanthan Gum (0.1) | — | — | — | syringe |
| 85 | PFP (1) | Pol F68 (200) | — | — | Simeth (500) | Xanthan Gum (0.1) | — | — | — | syringe |
| 86 | PFP (1) | — | — | — | — | Methyl Cellulose (0.1) | — | — | — | syringe |
| 87 | PFP (1) | Pol F68 (200) | — | — | Simeth (500) | Xanthan Gum (0.1) | — | — | — | syringe |
| 88 | PFP (1) | Pol F68 (200) | — | — | Simeth (500) | Xanthan Gum (0.1) | — | — | — | syringe |
| 89 | PFP (1) | Pol F68 (200) | Zonyl ™ FSN (100) | — | Simeth (500) | Xanthan Gum (0.2) | — | — | — | syringe |
| 90 | — | Pol F68 (200) | — | — | Simeth (500) | Xanthan Gum (0.2) | — | — | — | syringe |
| 91 | — | Pol F68 (200) | Zony ™ FSN (100) | — | Simeth (500) | Xanthan Gum (0.2) | — | — | — | syringe |

TABLE 3-continued

Example 12

| Example No. | Gaseous Precursor (%) | Stabilizing Material | | | Dispersing Agent (ppm) | Thickening Agent (%) | Auxiliary Materials | | | Agitating Method |
|---|---|---|---|---|---|---|---|---|---|---|
| | | Surfactant (A) (ppm) | Surfactant (B) (ppm) | Surfactant (C) (ppm) | | | Oils (%) | Preservative (ppm) | Sweetening Agent | |
| 92 | PFP (1) | — | — | — | — | Hyaluronic Acid (0.2) | — | — | — | syringe |
| 93 | PFP (1) | — | — | — | — | Xanthan Gum (0.2) | — | — | — | syringe |
| 94 | PFP (1) | PS 40 (100) | — | — | — | Xanthan Gum (0.2) | — | — | — | syringe |
| 95 | PFP (1) | PS 40 (100) | — | — | Simeth (100) | Xanthan Gum (0.2) | — | — | — | syringe |
| 96 | PFP (1) | Pol F68 (100) | — | — | — | Xanthan Gum (0.2) | — | — | — | syringe |
| 97 | PFP (1) | Pol F68 (100) | — | — | Simeth (100) | Xanthan Gum (0.2) | — | — | — | syringe |
| 98 | PFP (1) | — | PS 40 (100) | — | Simeth (100) | Xanthan Gum (0.2) | — | — | — | Microfluidize |
| 99 | PFP (1) | Pol F68 (100) | PS 40 (100) | — | Simeth (100) | Xanthan Gum (0.2) | — | — | — | Microfluidize |
| 100 | PFP (1) | Pol F68 (100) | PS 40 (100) | — | Simeth (500) | Xanthan Gum (0.2) | — | — | — | Microfluidize |
| 101 | PFP (1) | Pol F68 (100) | PS 40 (100) | — | Simeth (500) | Xanthan Gum 0.4 | — | — | — | Microfluidize |
| 102 | PFP (1) | Pol F68 (100) | PS 40 (100) | — | Simeth (500) | — | — | — | — | Microfluidize |
| 103 | PFP (1) | Pol F68 (100) | PS 40 (100) | — | Simeth (500) | Xanthan Gum (0.2) Methyl Cellulose (0.25) | — | — | — | Microfluidize |
| 104 | PFP (1) | — | — | — | — | Methyl Cellulose (0.25) | — | — | — | Microfluidize |
| 105 | PFP (1) | Pol F68 (100) | — | — | Simeth (200) | Methyl Cellulose (1) | — | — | — | Microfluidize |
| 106 | PFP (1) | Pol F68 (100) | — | — | Simeth (200) | Xanthan Gum Methyl Cellulose (0.1) | — | — | — | Microfluidize |
| 107 | PFP (1) | Pol F68 (100) | — | — | Simeth (200) | Xanthan Gum (0.2) Methyl Cellulose (1) | — | — | — | Microfluidize |
| 108 | PFP (1) | — | — | — | — | Methyl Cellulose (1) | — | — | — | syringe |
| 109 | PFP (1) | — | — | — | — | Agarose (0.1) | — | — | — | Microfluidize |
| 110 | PFP (1) | — | — | — | — | Agarose 0.4 | — | — | — | syringe |
| 111 | PFP (1) | — | — | — | — | — | — | — | — | Microfluidize |
| 112 | PFP (1) | — | — | — | — | — | — | — | — | Microfluidize |
| 113 | PFP (1) | — | — | — | — | Veegum (1) | — | — | — | syringe |
| 114 | PFP (1) | — | — | — | — | Veegum (5) | — | — | — | Microfluidize |
| 115 | PFP (1) | — | — | — | — | Alginic Acid (1) | — | — | — | Microfluidize |
| 116 | PFP (1) | — | — | — | — | Xanthan Gum (0.2)** | — | — | — | Microfluidize |
| 117 | PFP (1) | — | — | — | — | — | — | Sorbate (100) | — | Microfluidize |
| 118 | PFP (1) | Pol F68 (100) | PS 40 (100) | — | Simeth (500) | Methyl | — | — | — | Microfluidize |

TABLE 3-continued

Example 12

| Example No. | Gaseous Precursor (%) | Stabilizing Material Surfactant (A) (ppm) | Stabilizing Material Surfactant (B) (ppm) | Stabilizing Material Surfactant (C) (ppm) | Dispersing Agent (ppm) | Thickening Agent (%) | Oils (%) | Auxiliary Materials Preservative (ppm) | Auxiliary Materials Sweetening Agent | Agitating Method |
|---|---|---|---|---|---|---|---|---|---|---|
| 119 | PFP (1) | Pol F68 (100) | PS 40 (100) | — | Simeth (500) | Cellulose (1), Carboxymethyl cellulose (1) | — | Sorbate (100) | — | Microfluidize |
| 120 | PFP (1) | — | — | — | — | Mixture of Xanthan Gum and Carboxymethyl Cellulose | — | — | — | Microfluidize |
| 121 | PFP (1) | Pol F68 (100) | — | — | Simeth (500) | — | — | — | — | syringe |
| 122 | PFP (1) | Pol F68 (100) | — | — | Simeth (500) | — | — | — | — | syringe |
| 123 | PFP (1) | Pol F68 (100) | — | — | Simeth (500) | — | — | — | — | syringe |
| 124 | PFP (0.5), PFO (0.5) | Pol F68 (100) | — | — | Simeth (500) | — | — | — | — | syringe |
| 125 | PFP (1) | Pol F68 (100) | PS 40 (100) | Pol L61 (100) | Simeth (500) | — | — | — | — | syringe |
| 126 | PFP (1) | Pol F68 (500) | — | — | Simeth (500) | — | — | — | — | syringe |
| 127 | PFP (1) | Pol F68 (500) | — | — | Simeth (500) | Methyl Cellulose (0.25) | — | Benzoate (0.1) | — | Microfluidize |
| 128 | PFP (1) | Pol F68 (500) | — | — | Simeth (500) | Methyl Cellulose (0.25) | — | Benzoate (0.1) | — | Microfluidize |
| 129 | PFP (1) | Pol F68 (500) | — | — | Simeth (500) | Xanthan Gum (0.25) | — | Benzoate (0.1) | — | Microfluidize |
| 130 | PFP (1) | Pol F68 (500) | — | — | Simeth (500) | Methyl Cellulose (0.25) | — | Benzoate (0.1) | — | Microfluidize |
| 131 | PFP (1) | Pol F68 (500) | — | — | Simeth (500) | Methyl Cellulose (0.25) | — | Sorbate (0.1) | — | Microfluidize |
| 132 | PFP (1) | Pol F68 (500) | — | — | Simeth (500) | Methyl Cellulose (0.25) | — | Sorbate (0.1) | — | Microfluidize |
| 133 | PFP (1) | Pol F68 (500) | — | — | Simeth (500) | Xanthan Gum (0.25) | — | Sorbate (0.1) | — | Microfluidize |
| 134 | PFP (1) | Pol F68 (500) | — | — | Simeth (500) | — | — | Sorbate (0.1) | — | Microfluidize |
| 135 | PFP (0.1) | Pol F68 (100) | PS 40 (100) | — | Simeth (500) | Methyl Cellulose (0.25) | — | Sorbate (0.1) | — | Microfluidize |
| 136 | PFP (0.1) | Pol F68 (100) | PS 40 (100) | — | Simeth (500) | Methyl Cellulose (0.25) | — | Sorbate (0.1) | — | Microfluidize |
| 137 | PFP (0.1) | Pol F68 (100) | PS 40 (100) | — | Simeth (500) | Methyl Cellulose (0.25) | — | Sorbate (0.1) | — | Microfluidize |
| 138 | PFP (0.1) | Pol F68 (100) | PS 40 (100) | — | Simeth (500) | Methyl Cellulose (0.25) | — | Sorbate (0.1) | — | Microfluidize |
| 139 | PFP (1) | Pol F68 (100) | PS 40 (100) | — | Simeth (500) | Methyl Cellulose (0.25) | — | Benzoate (0.1) | — | Microfluidize |
| 140 | PFP (1) | Pol F68 (100) | PS 40 (100) | — | Simeth (500) | Xanthan Gum (0.25) | — | Benzoate (0.1) | — | Microfluidize |
| 141 | PFP (1) | Pol F68 (100) | PS 40 (100) | — | Simeth (500) | — | — | Benzoate (0.1) | — | Microfluidize |
| 142 | PFP (1) | Pol F68 (100) | PS 40 (100) | — | Simeth (500) | Methyl Cellulose (0.75) | — | Benzoate (0.1) | — | Microfluidize |
| 143 | PFP (1) | Pol F68 (500) | — | — | Simeth (500) | — | — | Benzoate (0.1) | — | Microfluidize |

TABLE 3-continued

Example 12

| Example No. | Gaseous Precursor (%) | Stabilizing Material Surfactant (A) (ppm) | Stabilizing Material Surfactant (B) (ppm) | Stabilizing Material Surfactant (C) (ppm) | Dispersing Agent (ppm) | Thickening Agent (%) | Oils (%) | Auxiliary Materials Preservative (ppm) | Auxiliary Materials Sweetening Agent | Agitating Method |
|---|---|---|---|---|---|---|---|---|---|---|
| 144 | PFP (1) | Pol F68 (500) | — | — | Simeth (500) | Methyl Cellulose (0.25) | — | Benzoate (0.1) | — | Microfluidize |
| 145 | PFP (1) | Pol F68 (500) | — | — | Simeth (500) | Xanthan Gum (0.25) | — | Benzoate (0.1) | — | Microfluidize |
| 146 | PFP (1) | Pot F68 (500) | — | — | Simeth (500) | — | — | Benzoate (0.1) | — | Microfluidize |
| 147 | PFP (1) | Pot F68 (500) | — | — | Simeth (500) | — | — | Benzoate (0.1) | — | Microfluidize |
| 148 | PFP (1) | Pol F68 (100) | PS 40 (100) | — | Simeth (500) | Methyl Cellulose (0.25) | — | Benzoate (0.1) | — | Microfluidize |
| 149 | PFP (1) | Pol F68 (500) | — | — | Simeth (500) | Xanthan Gum (0.25) | — | Sorbate (0.1) | — | Microfluidize |
| 150 | PFP (1) | Pol F68 (100) | PS 40 (100) | — | Simeth (500) | Xanthan Gum (0.25) | — | Sorbate (0.1) | — | Microfluidize |
| 151 | PFP (1) | Pol F68 (500) | — | — | Simeth (500) | Methyl Cellulose (0.5) | — | Benzoate (0.1) | LART | L4RT |
| 152 | PFP (1) | Pol F68 (500) | PS 40 (100) | PG*** | Simeth (500) | Methyl Cellulose (0.5) | — | Benzoate (0.1) | — | Microfluidize |
| 153 | PFP (1) | Pol F68 (500) | PS 40 (100) | — | Simeth (500) | Methyl Cellulose (0.5) | — | Benzoate (0.1) | — | Microfluidize |
| 154 | PFP (1) | Pol F68 (500) | PS 40 (100) | PG**** | Simeth (500) | Methyl Cellulose (0.5) | — | Benzoate (0.1) | Fructose (0.2)M | Microfluidize |
| 155 | PFP (1) | Pol F68 (500) | PS 40 (100) | — | Simeth (500) | Methyl Cellulose (0.5) | — | Benzoate (0.1) | — | Microfluidize |
| 156 | PFP (1) | Pol F68 (500) | PS 40 (100) | — | Simeth (500) | Methyl Cellulose (0.5) | — | Benzoate (0.1) | Fructose (1)M | Microfluidize |
| 157 | PFP (1) | Pol F68 (500) | PS 40 (100) | — | Simeth (500) | Methyl Cellulose (0.5) | — | Benzoate (0.1) | Fructose 2 | L4RT |
| 158 | PFP (1) | Pol F68 (500) | PS 40 (100) | — | Simeth (500) | Kelgum (0.25) | — | Benzoate (0.1) | Fructose 2 | L4RT |
| 159 | PFP (1) | Pol F68 (500) | PS 40 (100) | — | Simeth (500) | GP209 (0.25) | — | Benzoate (0.1) | Fructose 2 | L4RT |
| 160 | PFP (1) | Pol F68 (500) | PS 40 (100) | — | Simeth (500) | Methyl Cellulose (0.5) | — | Benzoate (0.1) | Fructose 2 | Microfluidize |
| 161 | PFP (1) | Pol F68 (500) | PS 40 (100) | — | Simeth (500) | Methyl Cellulose (0.5) | — | Benzoate (0.1) | Fructose 2 | L4RT |
| 162 | PFP (1) | Pol F68 (500) | PS 40 (100) | — | Simeth (500) | Veegum (1) | — | Benzoate (0.1) | Fructose 2 | L4RT |
| 163 | PFP (1) | Pol F68 (500) | PS 40 (200) | — | Simeth (500) | Xanthan Gum (1) | — | Benzoate (0.1) | Fructose 2 | L4RT |
| 164 | PFP (1) | Pol F68 (500) | PS 40 (200) | — | Simeth (500) | — | — | Benzoate (0.1) | Fructose 2 | L4RT |
| 165 | PFP (1) | Pol F68 (500) | PS 40 (200) | — | Simeth (500) | Xanthan Gum (0.5) | — | Benzoate (0.1) | Fructose 2 | L4RT |
| 166 | PFP (1) | Pol F6S (500) | PS 40 (200) | — | Simeth (500) | Methyl Cellulose (0.75) | — | Benzoate (0.1) | Fructose 2 | L4RT |

*1% concentration
**coated with 1% simethicone

TABLE 3-continued

Example 12

| Example No. | Gaseous Precursor (%) | Stabilizing Material | | | Dispersing Agent (ppm) | Thickening Agent (%) | Oils (%) | Auxiliary Materials | | Agitating Method |
|---|---|---|---|---|---|---|---|---|---|---|
| | | Surfactant (A) (ppm) | Surfactant (B) (ppm) | Surfactant (C) (ppm) | | | | Preservative (ppm) | Sweetening Agent | |

***200 nM concentration
****1M concentration
KEY
PFP = perfluoropentane
PFA = perfluorohexane
PFO = perfluorooctane
SLS = sodium lauryl sulfate
Pol = poloxamer
PS = polysorbate
CTAB = cetyltrimethylammonium bromide
Simeth = simethicone

EXAMPLE 168

This example describes comparative imaging studies involving the stabilized suspensions of the present invention and prior art contrast agents.

Methylcellulose (2.5 g), poloxamer F68 (0.25 g), simethicone (0.25 g), polysorbate 40 (0.1 g), fructose (10 g), sodium benzoate (0.5 g) (Spectrum Houston Tex.) and purified water (486 mL) were combined and the resulting mixture was mixed until homogenous using a Silverson L4RT mixer equipped with the 1" tubular assembly and the square hole high-shear screen set at 8000 rpm. The homogenous mixture was cooled to 4° C. in an ice bath and perfluoropentane (3 mL) was added. The resulting mixture was homogenized by mixing for 1 minute using the same mixer and assembly as above, set at a higher speed (12,000 rpm).

Four 250 g Sprague-Dawley rats (rats (A), (B), (C) and (D)) were administered the stabilized suspension prepared above, contrast agent of the prior art, and mixtures of the above suspension and contrast agent of the prior art. Rat (A), which had been NPO for 24 hr, was gavaged with the stabilized suspension prepared above. Rat (B) was gavaged with Scan C™ (4 mL) (Smith and Nephew Diagnostics, Memphis, Tenn.) which is a prior art, barium sulfate contrast agent. Rat (C) was gavaged with a mixture (4 mL) of the stabilized suspension prepared above to which 0.2% by weight barium sulfate had been added. Rat (D) was gavaged with Scan C™ (2 mL) followed by a second gavage one hour later with the stabilized suspension prepared above. All of the rats were imaged at 1.25 and 2.25 hours after administration on a Somotom DRH (Iselin, N.J.) with settings of TI 3, KVp 125, AS 0.28, Slice thickness 4 mm, and a Gantly tilt of 0. The images obtained of rat (A) were homogeneous and black throughout the GI tract. The images obtained of rat (B) showed sequestering of the barium sulfate contrast. The images obtained for rat (C) showed sequestered barium sulfate (positive contrast) mixed with areas of negative contrast (i.e. a two phase contrast). The images obtained of rat (D) were undifferentiated from those of rat (A) at 1.25 hours; however, the barium sulfate sequestered in the lower bowel at 2.25 hours.

EXAMPLE 169

This example describes a preliminary toxicity study which were conducted on stabilized suspensions within the scope of the present invention. The studies involved comparing the toxicity of the present suspensions with the toxicity of a control (mixtures prepared without a gas or gaseous precursor).

Preparation of Stabilized Suspension

Into a 15 mL polypropylene screw cap tube (VWR, West Chester, Pa.) were introduced water (7.3 mL), 1% xanthan gum (1 mL), soy oil (1 mL), a 1% aqueous solution of sodium lauryl sulfate (300 µL) (Duponol C, Witco Corp., New York, N.Y.), a 1% aqueous solution of Polysorbate 40 (200 µL), a 1% aqueous solution of potassium sorbate (100 µL), simethicone (5 µL), and perfluoropentane (100 µL). This mixture was mixed for 1 minute using a Vortex-Genie 2 (Scientific Industries Inc., Franklin Lakes, N.J.) on full speed to produce a homogeneous mixture.

Preparation of Control Mixture

A mixture was prepared as described above except there was no perfluoropentane. This is referred to herein as "the control mixture".

Toxicity Study

Twelve Sprague-Dawley rats (250 to 300 g) were used in the toxicity study and were divided into three groups (Groups (A), (B) and (C)) of four rats each. The rats of Group (A) were dosed with the control mixture (4 mL) once a day for seven days. The rats of Group (B) were dosed with the stabilized suspension prepared above (4 mL) once a day for seven days. The rats of Group (C) were dosed with the stabilized suspension prepared above (3 mL) twice a day. After four days, the second daily dose which was being administered to the Group (C) rates was discontinued due to excessive irritation of the esophagi from the gavage tubes. The Group (C) rats were then dosed with a single daily dose (4 mL) for the remaining three days. No substantial differences were observed in the food consumption or the weights of the rats of Groups (A), (B) and (C). The rats were sacrificed after the seven day treatment period and blood and tissue samples were collected. Blood chemistry analysis showed no significant differences among the rats of Groups (A), (B) and (C). In addition, tissue samples of multiple organs showed no significant differences or toxicity indications among the rats of Groups (A), (B) and (C). A possible renal tubular epithelium degeneration in the collecting ducts of the rats of Group C was observed. However, it is believed that this was due to the advanced age of the rats studied in Group C.

The following examples, (Examples 170 to 177) are hypothetical examples and describe the various clinical applications of the stabilized suspensions of the present invention.

EXAMPLE 171

This example describes the use of the present stabilizing suspensions in magnetic resonance angiography (MRA).

In a patient suffering from abdominal disease, 10 mL/kg of the stabilized suspension prepared in Example 1 will be administered orally. Magnetic resonance (MR) imaging will be performed obtaining axial T1 and T2 weighted images. The bowel will appear homogeneously with low signal intensity as a signal void. MR angiography (MRA) of the abdominal vasculature will be performed also using a 2D Time of Flight pulse sequence, axial acquisition. The MRA image will be of high quality, with no discernible artifacts caused by the stabilized suspension of the present invention.

Two comparative MRA studies will be conducted to evaluate the efficacy of the stabilized suspensions of the present invention. In the first comparative study, patients will be administered orally a positive GI MR contrast agent, such as dilute (4 millimolar) gadolinium diethylenetriamine pentaacetic acid (Gd-DTPA). MRA images will be degraded by ghosting artifacts from the high signal intensity in the bowel lumen. In the second comparative study, a patient will be administered iron oxide particles as a GI contrast medium. MRA images will be degraded by susceptibility artifacts. These studies will show that the stabilized suspensions of the present invention provide excellent GI contrast and are also effective as adjuncts for MRA in the abdomen or pelvis.

EXAMPLE 172

This example describes the use of the stabilized suspensions of the present invention for improving the CT imaging characteristics of prior art positive contrast agents.

60% Hypaque™ iodinated contrast media (300 mL) will be combined with a stabilized suspension of perfluoropentane (600 mL) within the scope of the present invention. The suspension will preferably comprise perfluoropentane filled microspheres. The concentration of Hypaque™ in the resulting "combination" contrast medium will be 20% by volume and the concentration of perfluoropentane filled microspheres will be 1% by volume. The contrast medium will be administered orally to a patient at a dose of 15 mL/kg. After ingestion, the perfluoropentane will be converted to a gas and the overall volume of the contrast medium will expand. This expansion will result in controlled and uniform distension of the GI tract with homogenous high density. Improved definition of the mucosal surfaces in the GI tract will be observed with the combination contrast medium, as compared to Hypaque™ alone. This improved definition is due to distension of the GI tract caused by the stabilized suspension of the present invention.

EXAMPLE 173

This example describes the use of the stabilized suspensions of the present invention for improving the CT and X-ray imaging characteristics of prior art contrast agents.

A patient will be administered a 0.4% by weight composition of barium sulfate (400 mL) that is designed to adhere to the mucosal surfaces of the bowel. Preparation of the barium sulfate composition will involve grinding barium sulfate in a colloid mill with a carrageenan powder. The resulting micron-sized particles of barium sulfate coated with carrageenan are designed to have an affinity for the mucosal surfaces of the bowel. Four hours after administration, the patient will be administered a stabilized suspension of the present invention (15 mL/kg). The administration of both barium sulfate and a stabilized suspension of the present invention will provide a double contrast examination of the bowel for computed tomography or fluoroscopy. The mucosal surfaces of the bowel will be highlighted with a fine, thin layer of high density and the lumen will be black.

EXAMPLE 174

This example describes the use of the stabilized suspensions of the present invention for improving the MR imaging characteristics of prior art contrast agents.

A patient will be administered of Luminance™ (400 mL) (Bracco Diagnostics, Princeton, N.J.) which contains manganese chloride ($MgCl_2$) in admixture with polygalacturonic acid. Four hours after administration, the patient will be administered a stabilized suspension of the present invention (15 mL/kg). MR imaging will be performed on a commercial MR imager with T1 weighted spin echo technique, for example, where TR is 300 msec and TE is 11 msec. The resulting images will show a two phase contrast. Due to the administration of the stabilized suspension of the present invention, the lumen of the bowel will be homogeneously dark and will appear as a signal void. The mucosal surface will appear as a thin, bright rim. Mucosal surfaces are thereby highlighted with a dual contrast MR technique.

EXAMPLE 175

This example describes the use of the stabilized suspensions of the present invention for improving the MR imaging characteristics of prior art contrast agents administered by I.V.

A stabilized suspension of the present invention is administered (20 mL/kg) over a two hour period to a patient suffering from polyps in the bowel. Ten minutes prior to scanning with MR, 500 millimolar solution of Gd-DTPA (Schering A. G., Berlin, Germany), providing a dose of 0.1 mL/kg, will be administered I.V. T1 weighted MR images will be obtained with parameters as described above in Example 170 except that fat saturation will be used also with imaging on a 1.5 Tesla magnet. The resulting MR images will show the polyps as high signal, contrast enhancing structures within a black background. Accordingly, improved conspicuity of the polyps will be obtained. The resulting pattern of contrast will be useful for detecting a variety of neoplasms arising throughout the GI tract. With genetic screening, this will be a useful surveillance technique for patients with oncogenes at risk for development of GI tract neoplasms.

EXAMPLE 176

A study similar to that conducted in Example 175 will be repeated except that the patient will be administered 0.010 millimoles/kg of a compound containing manganese, for example, manganese dipyridoxaldiphosphate (Nycomed, Oslo, Norway) instead of the gadolinium compound. As with the results obtained in Example 171, areas of abnormal mucosa throughout the GI tract will be readily apparent as contrast enhancing lesions on MR.

EXAMPLE 177

This example describes the use of the stabilized suspensions of the present invention in connection with targeted, positive contrast agents.

A contrast agent comprising a targeted paramagnetic or radiodense agent, for example, $MnCl_2$ nanogels (100 mg) labelled with an antibody for carcinoembryonic antigen, or barium sulfate particles (1 g) labelled with endothelial growth factor, will be administered to a patient suffering from cancer of the GI tract. Twenty-four hours after administration of the aforesaid targeted contrast agent, the patient will be administered 20 mL/kg of a stabilized suspension of the present invention. CT or MR imaging will be performed. The bowel will appear black and an area of carcinoma will be detected within the bowel as a bright spot superimposed upon the black background.

The disclosures of each patent, patent application and publication cited or described in this document are hereby incorporated by reference, in their entirety.

Various modifications of the invention, in addition to those described herein, will be apparent to those skilled in the art from the foregoing description. Such modifications are also intended to fall within the scope of the appended claims.

What is claimed:

1. A method of providing an image of an internal region of a patient comprising (i) administering to the patient a stabilized, substantially homogeneous, aqueous suspension of a gaseous precursor, (ii) allowing said gaseous precursor to undergo a phase transition from a liquid to a gas in vivo, and (iii) scanning the patient using computed tomography to obtain visible images of the region, wherein said gaseous precursor comprises a perfluorocarbon and said suspension is in the form of an emulsion.

2. A method according to claim 1 wherein said gaseous precursor undergoes a phase transition from a liquid to a gaseous state at near the normal body temperature of the patient.

3. A method according to claim 1 wherein said suspension has a negative density of about −40 HU or less.

4. A method according to claim 3 wherein said suspension has a negative density of about −50 HU or less.

5. A method according to claim 4 wherein said suspension has a negative density of about −100 HU or less.

6. A method according to claim 5 wherein said suspension has a negative density of about −500 HU or less.

7. A method according to claim 1 wherein said suspension is stabilized with a stabilizing material.

8. A method according to claim 7 wherein said stabilizing material comprises a surfactant.

9. A method according to claim 8 wherein said surfactant is selected from the group consisting of anionic, cationic, zwitterionic and nonionic surfactants.

10. A method according to claim 9 wherein said surfactant comprises a nonionic surfactant.

11. A method according to claim 10 wherein said nonionic surfactant is selected from the group consisting of a polyoxyethylene-polyoxypropylene glycol block copolymer and a sorbitan fatty acid ester.

12. A method according to claim 11 wherein said perfluorocarbon is selected from the group consisting of perfluoropentane, perfluorohexane, perfluoroheptane and perfluorooctane.

13. A method according to claim 12 wherein said perfluorocarbon comprises perfluoropentane.

14. A method according to claim 1 wherein said suspension further comprises a thickening agent.

15. A method according to claim 14 wherein said thickening agent is selected from the group consisting of starches, gums, pectin, casein, agarose, gelatin, carrageenan and cellulose derivatives.

16. A method according to claim 15 wherein said thickening agent is selected from the group consisting of gums, carrageenan and cellulose additives.

17. A method according to claim 16 wherein said gum comprises xanthan gum.

18. A method according to claim 16 wherein said cellulose derivative is selected from the group consisting of methyl cellulose and carboxymethyl cellulose.

19. A method according to claim 18 wherein said cellulose derivative comprises methyl cellulose.

20. A method according to claim 1 wherein said suspension further comprises a dispersing agent.

21. A method according to claim 20 wherein said dispersing agent comprises a polymeric siloxane compound.

22. A method according to claim 21 wherein said polymeric siloxane compound is substantially completely alkylated with alkyl groups.

23. A method according to claim 22 wherein said alkyl groups comprise lower alkyl groups.

24. A method according to claim 23 wherein said lower alkyl groups are methyl groups.

25. A method according to claim 24 wherein said polymeric siloxane compound is $\alpha$-(trimethylsilyl)-$\omega$-methylpoly[oxy(dimethylsilylene)].

26. A method according to claim 1 wherein said suspension further comprises a compound selected from the group consisting of lipids, ingestible oils, viscosity modifiers, emulsifying and/or solubilizing agents, suspending or viscosity-increasing agents, synthetic suspending agents, and tonicity-raising agents.

27. A method according to claim 1 wherein the region comprises the vasculature region.

28. A method according to claim 1 wherein the region comprises the cardiovascular region.

29. A method according to claim 1 wherein the region comprises the gastrointestinal region.

30. A method according to claim 1 wherein said scanning is of a region of a patient selected from the group consisting of the intranasal tract, the auditory canal, the intraocular region, the intraperitoneal region, the kidneys, the urethra and the genitourinary tract.

31. A method for diagnosing the presence of diseased tissue in a patient comprising (i) administering to the patient a stabilized, substantially homogeneous, aqueous suspension of a gaseous precursor, (ii) allowing said gaseous precursor to undergo a phase transition from a liquid to a gas in vivo, and (iii) scanning the patient using computed tomography to obtain visible images of any diseased tissue in the patient, wherein said gaseous precursor comprises a perfluorocarbon and said suspension is in the form of an emulsion.

* * * * *